United States Patent [19]

Basha et al.

[11] Patent Number: 5,616,596

[45] Date of Patent: Apr. 1, 1997

[54] SUBSTITUTED ARYLALKYNYL-AND HETEROARYLALKYNL-N-HYDROXYUREA INHIBITORS OF LEUKOTRIENE BIOSYNTHESIS

[75] Inventors: Anwer Basha, Lake Forest; Clint D. W. Brooks; Pramila Bhatia, both of Libertyville, all of Ill.; Richard A. Craig, Racine, Wis.; James D. Ratajczyk, Waukegan; Andrew O. Stewart, Libertyville, both of Ill.

[73] Assignee: Abbott Laboratories, Abbott Park, Ill.

[21] Appl. No.: 416,807

[22] PCT Filed: Nov. 5, 1993

[86] PCT No.: PCT/US93/10675

§ 371 Date: Apr. 13, 1995

§ 102(e) Date: Apr. 13, 1995

[87] PCT Pub. No.: WO94/11342

PCT Pub. Date: May 26, 1994

Related U.S. Application Data

[63] Continuation-in-part of Ser. No. 973,100, Nov. 6, 1992, Pat. No. 5,288,751.

[51] Int. Cl.⁶ .................. A61K 31/42; A61K 31/425; C07D 263/30; C07D 277/20
[52] U.S. Cl. .................. 514/365; 514/369; 514/374; 514/376; 548/182; 548/202; 548/204; 548/225; 548/235
[58] Field of Search ................ 549/62, 77, 475, 549/491, 438, 446, 471, 473; 548/182, 202, 204, 225, 235; 514/365, 369, 374, 376, 438, 446, 471, 473

[56] References Cited

U.S. PATENT DOCUMENTS

| | | | |
|---|---|---|---|
| 4,738,986 | 4/1988 | Kneen et al. | 514/575 |
| 5,214,204 | 5/1993 | Dellaria et al. | 562/623 |
| 5,288,751 | 2/1994 | Brooks et al. | 514/438 |

FOREIGN PATENT DOCUMENTS

| | | |
|---|---|---|
| 0468281 | 10/1991 | European Pat. Off. . |
| 9201682 | 2/1992 | WIPO . |
| 9210469 | 6/1992 | WIPO . |

OTHER PUBLICATIONS

Chemical Abstracts, vol. 117(3), issued 20 Jul. 1992, (Columbus, Ohio), Brooks et al., "Preparation . . . Inhibitors", see Abstract 263466, WO-92-01,682, 06 Feb. 1992.

Chemical Abstracts, vol. 117(15), issued 12 Oct. 1992, (Columbus, Ohio), Ardo et al., "Preparation . . . Inhibitors", see abstract 263,466q, WO-92 10,469, 25 Jun. 1992.

*Primary Examiner*—Alan L. Rotman
*Attorney, Agent, or Firm*—Monte R. Browder

[57] ABSTRACT

The invention relates to compounds having activity to inhibit lipoxygenase enzyme activity, to pharmaceutical compositions comprising these compounds, and to a medical method of treating. More particularly, this invention concerns certain substituted arylalkynyl- and ((heteroaryl)alkynyl)-N-hydroxy-ureas which inhibit leukotriene biosynthesis, to pharmaceutical compositions of these compounds and to a method of inhibiting leukotriene biosynthesis.

4 Claims, No Drawings

SUBSTITUTED ARYLALKYNYL-AND HETEROARYLALKYNL-N-HYDROXYUREA INHIBITORS OF LEUKOTRIENE BIOSYNTHESIS

CROSS-REFERENCES TO RELATED APPLICATIONS

This application is a 371 of PCT/US 93/10675 filed Nov. 5, 1993 and a continuation-in-part of application Ser. No. 07/973,100 filed Nov. 6, 1992, now U.S. Pat. No. 5,288,751.

TECHNICAL FIELD

This invention relates to compounds having activity to inhibit lipoxygenase enzyme activity, to pharmaceutical compositions comprising these compounds, and to a medical method of treatment. More particularly, this invention concerns certain substituted arylalkynyl- and ((heteroaryl)alkynyl)-N-hydroxyureas which inhibit leukotriene biosynthesis, to pharmaceutical compositions comprising these compounds and to a method of inhibiting leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or convened to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

U.S. Pat. No. 4,738,986 to Kneen, et al. discloses and claims N-(3-phenoxycinnamyl)acetohydroxamic acid, its salts and related compounds having utility for inhibiting lipoxygenase and cyclooxygenase enzymes.

European Patent Application 299 761 to Salmon, et al. discloses and claims certain (substituted phenoxy)phenylalkenyl hydroxamic acids and their salts which are useful as agents for inhibiting lipoxygenase and cyclooxygenase activity.

European Patent Application (Case number 4824) to Brooks, et al. discloses and claims certain substituted alkynyl ureas and hydroxamic acid, which do not contain spacer groups, having lipoxygenase inhibiting activity.

SUMMARY OF THE INVENTION

In its principal embodiment, the present invention provides certain N-[((substituted)aryl)alkynyl]- and N-[((substituted)heteroary)alkynyl]-N-hydroxyurea compounds which inhibit 5-lipoxygenase enzyme activity and thus leukotriene biosynthesis and are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

The present invention provides a compound of the structure

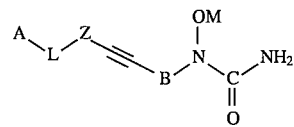

or a pharmaceutically acceptable salt thereof where M represents hydrogen, a pharmaceutically acceptable cation, or a pharmaceutically acceptable metabolically cleavable group.

B is a straight or branched divalent alkylene group of one to twelve carbon atoms.

Z is selected from the group consisting of (a) phenyl, optionally substituted with alkyl of one to six carbon atoms, haloalkyl of one to six carbon atoms, alkoxy of one to twelve carbon atoms, or halogen, (b) furyl, optionally substituted with alkyl of one to six carbon atoms, or haloalkyl of one to six carbon atoms, (c) thienyl, optionally substituted with alkyl of one to six carbon atoms, or haloalkyl of one to six carbon atoms, (d) thiazolyl, optionally substituted with alkyl of one to six carbon atoms or haloalkyl of one to six carbon atoms, and (e) oxazolyl, optionally substituted with alkyl of one to six carbon atoms or haloalkyl of one to six carbon atoms.

L is selected from the group consisting of (a) alkylene of one to six carbon atoms, (b) alkenylene of one to six carbon atoms, (c) alkynylene of one to six carbon atoms, (d) hydroxyalkyl of one to six carbon atoms, (e) >C=O, (f) >C=N—$OR_1$, wherein $R_1$ is hydrogen or $C_1$–$C_6$ alkyl, (g) —$(CHR_1)_n(CO)(CHR_2)_m$, where n and m are independently selected from an integer from one to six and $R_1$ and $R_2$ are independently selected from hydrogen or $C_1$–$C_6$ alkyl, (h)

—(CHR$_1$)$_n$C=NOR$_2$, (i) —(CHR$_1$)$_n$ON=CR$_2$, (j) —(CHR$_1$)$_n$—O—(CHR$_2$)$_m$—, (k) —(CHR$_1$)$_n$—NR$_2$(CHR$_3$)$_m$—, where R$_3$ is selected from hydrogen or C$_1$–C$_6$-alkyl, (l) —(CHR$_1$)$_n$—S—(CHR$_2$)$_m$—, and (m) —(CHR$_1$)$_n$—(SO$_2$)—(CHR$_2$)$_m$—.

A is selected from the group consisting of (a) carbocyclic aryl optionally substituted with (a-1) alkyl of one to six carbon atoms, (a-2) haloalkyl of one to six carbon atoms, (a-3) hydroxyalkyl of one to six carbon atoms, (a-4) alkoxy of one to twelve carbon atoms, (a-5) alkoxyalkoxyl in which the two alkoxy portions may each independently contain one to six carbon atoms, (a-6) alkylthio of one to six carbon atoms, (a-7) hydroxy, (a-8) halogen, (a-9) cyano, (a-10) ammo, (a-11) alkylamino of one to six carbon atoms, (a-12) dialkylamino in which the two alkyl groups may independently contain one to six carbon atoms, (a-13) alkanoylamino of two to eight carbon atoms, (a-14) N-alkanoyl-N-alkylamino in which the alkanoyl may contain two to eight carbon atoms and the alkyl groups may contain one to six carbon atoms, (a-15) alkylaminocarbonyl of two to eight carbon atoms, (a-16) dialkylaminocarbonyl in which the two alkyl groups may independently contain one to six carbon atoms, (a-17) carboxyl, (a-18) alkoxycarbonyl of two to eight carbon atoms, (a-19) phenyl, optionally substituted with alkyl of one to six carbon atoms, haloalkyl of one to six carbon atoms, alkoxy of one to six carbon atoms, hydroxy or halogen, (a-20) phenoxy, optionally substituted with alkyl of one to six carbon atoms, haloalkyl of one to six carbon atoms, alkoxy of one to six carbon atoms, hydroxy or halogen, (a-21) phenylthio, optionally substituted with alkyl of one to six carbon atoms, haloalkyl of one to six carbon atoms, alkoxy of one to six carbon atoms, hydroxy or halogen, (a-22) pyridyl, optionally substituted with alkyl of one to six carbon atoms, haloalkyl of one to six carbon atoms, alkoxy of one to six carbon atoms, hydroxy or halogen, (a-23) pyridyloxy, optionally substituted with alkyl of one to six carbon atoms, haloalkyl of one to six carbon atoms, alkoxy of one to six carbon atoms, hydroxy or halogen; (b) furyl, optionally substituted with (b-1) alkyl of one to six carbon atoms, (b-2) haloalkyl of one to six carbon atoms, (b-3) halogen, (b-4) phenyl, optionally substituted with alkyl of one to six carbon atoms, haloalkyl of one to six carbon atoms, alkoxy of one to six carbon atoms, hydroxy or halogen, (b5) phenoxy, optionally substituted with alkyl of one to six carbon atoms, haloalkyl of one to six carbon atoms, alkoxy of one to six carbon atoms, hydroxy or halogen, (b-6) phenylthio, optionally substituted with alkyl of one to six carbon atoms, haloalkyl of one to six carbon atoms, alkoxy of one to six carbon atoms, hydroxy or halogen, (b-7) pyridyl, optionally substituted with alkyl of one to six carbon atoms, haloalkyl of one to six carbon atoms, alkoxy of one to six carbon atoms, hydroxy or halogen, (b-8) pyridyloxy, optionally substituted with alkyl of one to six carbon atoms, haloalkyl of one to six carbon atoms, alkoxy of one to six carbon atoms, hydroxy or halogen, (c) benzo[b]furyl, optionally substituted with (c-1) alkyl of one to six carbon atoms, (c-2) haloalkyl of one to six carbon atoms, (c-3) alkoxyl of one to six carbon atoms, (c-4) hydroxy, or (c-5) halogen; (d) thienyl, optionally substituted with (d-1) alkyl of one to six carbon atoms, (d-2) phenyl, optionally substituted with alkyl of one to six carbon atoms, haloalkyl of from one to six carbon atoms, alkoxy of from one to six carbon atoms, hydroxy, or halogen, (d-3) phenoxy, optionally substituted with alkyl of one to six carbon atoms, haloalkyl of one to six carbon atoms, alkoxy of one to six carbon atoms, hydroxy or halogen, (d-4) phenylthio, optionally substituted with alkyl of one to six carbon atoms, haloalkyl of one to six carbon atoms, alkoxy of one to six carbon atoms, hydroxy or halogen, (d-5) pyridyl, optionally substituted with alkyl of one to six carbon atoms, haloalkyl of one to six carbon atoms, alkoxy of one to six carbon atoms, hydroxy or halogen, (d-6) pyridyloxy, optionally substituted with alkyl of one to six carbon atoms, haloalkyl of one to six carbon atoms, alkoxy of one to six carbon atoms, hydroxy or halogen; (e) thiazolyl, optionally substituted with (e-1) alkyl of one to six carbon atoms, (e-2) phenyl, optionally substituted with alkyl of one to six carbon atoms, haloalkyl of one to six carbon atoms, alkoxy of one to six carbon atoms, hydroxy, or halogen, (e-3) phenoxy, optionally substituted with alkyl of one to six carbon atoms, haloalkyl of one to six carbon atoms, alkoxy of one to six carbon atoms, hydroxy or halogen, (e-4) phenylthio, optionally substituted with alkyl of one to six carbon atoms, haloalkyl of one to six carbon atoms, alkoxy of one to six carbon atoms, hydroxy or halogen, (e-5) pyridyl, optionally substituted with alkyl of one to six carbon atoms, haloalkyl of one to six carbon atoms, alkoxy of one to six carbon atoms, hydroxy or halogen, (e-6) pyridyloxy, optionally substituted with alkyl of one to six carbon atoms, haloalkyl of one to six carbon atoms, alkoxy of one to six carbon atoms, hydroxy or halogen; (f) benzo[b]thienyl, optionally substituted with (f-1) alkyl of one to six carbon atoms, (f-2) haloalkyl of one to six carbon atoms, (e3) alkoxyl of one to six carbon atoms, (f-4) hydroxy, or (f-5) halogen; (g) pyridyl, optionally substituted with (g-1) alkyl of one to six carbon atoms, (g-2) haloalkyl of one to six carbon atoms, (g-3) alkoxyl of one to six carbon atoms, (g4) hydroxy, or (g-5) halogen; (h) quinolyl, optionally substituted with (h-1) alkyl of one to six carbon atoms, (h-2) haloalkyl of one to six carbon atoms, (h-3) alkoxyl of one to six carbon atoms, (h-4) hydroxy, or (h-5) halogen; (i) indolyl, optionally substituted with (i-1) alkyl of one to six carbon atoms, (i-2) haloalkyl of one to six carbon atoms, (i-3) alkoxyl of one to six carbon atoms, (i-4) hydroxy, or (i-5) halogen; (j) 1,2-dihydro-2-oxoquinolyl, optionally substituted with (j-1) alkyl of one to six carbon atoms, (j-2) haloalkyl of one to six carbon atoms, (j-3) alkoxyl of one to six carbon atoms, (j-4) hydroxy, or (j-5) halogen; and (k) 2-pyrrolidinon-1-yl, optionally substituted with (k-1) alkyl of one to six carbon atoms, (k-2) haloalkyl of one to six carbon atoms, (k-3) alkoxyl of one to six carbon atoms, (k4) hydroxy, or (k-5) halogen.

In another embodiment, he present invention also provides pharmaceutical compositions which comprise a therapeutically effective amount of compound of as defined above in combination with a pharmaceutically acceptable carrier.

In yet another embodiment, the present invention provides a method of inhibiting lipoxygenase enzyme activity and thereby leukotirene biosynthesis in a host mammal in need of such treatment comprising administering to a mammal in need of such treatment a therapeutically effective amount of a compound as defined above.

DETAILED DESCRIPTION

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the structure —NHR' wherein R' is alkyl, as previously defined, Examples of alkylamino include methylamino, ethylamino, iso-propylamino and the like.

The term "alkylaminocarbonyl" refers to an alkylamino group, as previously defined, attached to the parent molecular moiety through a carbonyl group. Examples of alkylaminocarbonyl include methylamino-carbonyl, ethylaminocarbonyl, iso-propylaminocarbonyl and the like.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkanoyl" represents an alkyl group, as defined above, attached to the parent molecular moiety through a carbonyl group. Alkanoyl groups are exemplified by formyl, acetyl, propionyl, butanoyl and the like.

The term "alkanoylamino" refers to an alkanoyl group, as previously defined, attached to the parent molecular moiety through a nitrogen atom. Examples of alkanoylamino include formamido, acetamido, and the like.

The term "N-alkanoyl-N-alkylamino" refers to an alkanoyl group, as previously defined, attached to the parent molecular moiety through an aminoalkyl group. Examples of N-alkanoyl-N-alkylamino include N-methylformamido, N-methyl-acetamido, and the like.

The terms "alkoxy" or "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkoxyl" refers to an alkyl group, as defined above, attached through an oxygen to an alkyl group, as defined above, attached in turn through an oxygen to the parent molecular moiety. Examples of alkoxyalkoxyl include methoxymethoxyl, methoxyethyoxyl, ethoxyethoxyl and the like.

The term "alkoxyalkyl" refers to an alkoxy group, as defined above, attached through an alkylene group to the parent molecular moiety.

The term "alkoxycarbonyl" represents an ester group; i.e. an alkoxy group, attached to the parent molecular moiety through a carbonyl group such as methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynylene" refers to a divalent group derived by the removal of two hydrogen atoms from a straight or branched chain acyclic hydrocarbon group containing a carbon-carbon triple bond. Examples of alkynylene include —CH≡CH—, —CH≡CH—CH$_2$—, —CH≡CH—CH(CH$_3$)—, and the like.

The term "carbocyclic aryl" denotes a monovalent carbocyclic ring group derived by the removal of a single hydrogen atom from a monocyclic or bicyclic fused or non-fused ring system obeying the "4n+2 p electron" or Huckel aromaticity rule. Examples of carbocyclic aryl groups include phenyl, 1- and 2-naphthyl, biphenylyl, fluorenyl, and the like.

The term "(carbocyclic aryl)alkyl" refers to a carbocyclic aryl ring group as defined above, attached to the parent molecular moiety through an alkylene group. Representative (carbocyclic aryl)alkyl groups include phenylmethyl, phenylethyl, phenylpropyl, 1-naphthylmethyl, and the like.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moeity through a sulfur atom and thence through an alklyene group and are typified by phenylthiomethyl, 1- and 2-naphthylthioethyl and the like.

The term "dialkylamino" refers to a group having the structure -NR'R" wherein R' and R" are independently selected from alkyl, as previously defined. Additionally, R' and R" taken together may optionally be —(CH$_2$)$_{kk}$— where kk is an integer of from 2 to 6. Examples of dialkylamino include, dimethylamino, diethylaminocarbonyl, methylethylamino, piperidino, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "phenoxy" refers to a phenyl group attached to the parent molecular moiety through an oxygen atom.

The term "phenylthio" refers to a phenyl group attached to the parent molecular moiety through a sulfur atom.

The term "pyridyloxy" refers to a pyridyl group attached to the parent molecular moiety through an oxygen atom.

The term "metabolically cleavable group" denotes a group which is cleaved in vivo to yield the parent molecule of the structural formulae indicated above wherin M is hydrogen. Examples of metabolically cleavable groups include —COR, —COOR, —CONRR and —CH$_2$OR radicals where R is selected independently at each occurrence from alkyl, trialkylsilyl, carbocyclic aryl or carbocyclic aryl substituted with one or more of C$_1$–C$_4$ alkyl, halogen, hydroxy or C$_1$–C$_4$ alkoxy. Specific examples of representative metabolically cleavable groups include acetyl, methoxycarbonyl, benzoyl, methoxymethyl and trimethylsilyl groups.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, realate, maleate, malonate, methanesulfonate, 2-naphthalenesulfonate, nicotinate, nitrate, oleate, oxalate, palmitate, pamoate, pectinate, persulfate, 3-phenylpropionate, phosphate, pierate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention may exhibit stereoisomerism by virtue of the presence of one or more asymmetric or chiral centers in the compounds. The present invention contemplates the various stereoisomers and mixtures thereof. Desired enantiomers are obtained by chiral synthesis from commercially available chiral starting materials by methods well known in the art, or may be obtained from mixtures of the enantiomers by resolution using known techniques.

Compounds falling within the scope of the present invention include, but are not limited to:

N-{3-[5-(4-fluorophenylmethyl)fur-2-yl]-1-methyl-2-propynyl}-N-hydroxyurea,

N-{3-[5-(4-fluorophenylacetyl)fur-2-yl]-1-methyl-2-propynyl}-N-hydroxyurea,

N-{3-[5-(2-phenylethynyl)thien-2-yl]-1-methyl-2-propynyl}-N-hydroxyurea,

N-{3-[5-(2-[3-pyridyl]ethenyl)fur-2-yl]-1-methyl-2-propynyl}-N-hydroxyurea,

N-[3-{5-[2-(4-fluorophenyl]ethenyl)fur-2-yl]-1-methyl-2-propynyl}-N-hydroxyurea, N-{3-[5-(2-phenylethenyl)fur-2-yl]-1-methyl-2-propynyl}-N-hydroxyurea, N-{3-[5-(2-[2-pyridyl]ethenyl)fur-2-yl]-1-methyl-2-propynyl}-N-hydroxyurea, N-[3-{5-[2-(4-fluorophenyl)ethenyl]thien-2-yl}-1-methyl-2-propynyl]-N-hydroxyurea, N-[3-{5-[2-(5-methylphenyl)ethenyl]fur-2-yl}-3-butyn-2-yl]-N-hydroxyurea;

N-{3-[3-(O-benzyloxycarboxaldoxime)phenyl]-1-methyl-2-propynyl}-N-hydroxyurea,

N-{3-[(3-phenylcarbonyl)phenyl]-1-methyl-2-propynyl}-N-hydroxyurea;

N-{3-[5-(4-fluorophenylmethyl)thien-2-yl]-1-methyl-2-propynyl}-N-hydroxyurea, (R)-N-{3-[5-(4-fluorophenylmethyl)thien-2-yl]-1-methyl-2-propynyl}-N-hydroxyurea, N-{3-[5-(4-fluorophenylcarbonyl)thien-2-yl]-1-methyl-2-propynyl}-N-hydroxyurea, (R)-N-(3-(5-(4-fluorophenylcarbonyl)thien-2-yl)-1-methyl-2-propynyl)-N-hydroxyurea, N-{3-[5-(3-chloropyrid-3-ylmethyl)thien-2-yl]-1-methyl-2-propynyl}-N-hydroxyurea, (R)-N-{3-[5-(3-chloropyrid-3-ylmethyl)fur-2-yl]-1-methyl-2-propynyl}-N-hydroxyurea, (R)-N-{3-[5-(3-chloropyrid-3-ylmethyl)phenyl]-1-methyl-2-propynyl}-N-hydroxyurea, (R)-N-{3-[5-(4-chlorophenylmethyl)thien-2-yl]-1-methyl-2-propynyl}-N-hydroxyurea, (R)-N-{3-[5-(4-fluorophenylmethyl)thiazo-2-yl ]-1-methyl-2-propynyl}-N-hydroxyurea, (R)-N-(3-(5-(3-pyridylmethyl)thien-2-yl)-1-methyl-2-propynyl)-N-hydroxyurea, (R)-N-(3-(5-(4-fluorophenylmethyl)-4-methylthien-2-yl)-1-methyl-2-propynyl)-N-hydroxyurea, (R)-N-(3-(5-(2-ylmethyl)thien-2-yl)-1-methyl-2-propynyl)-N-hydroxyurea, (R)-N-(3-(5-(4-pyridylmethyl)thien-2-yl)-1-methyl-2-propynyl)-N-hydroxyurea, (R)-N-(3-(5-(2-naphthylmethyl)thien-2-yl)-1-methyl-2-propynyl)-N-hydroxyurea, (R)-N-(3-(5-(4-fluorophenylhydroxymethyl)thien-2-yl)-1-methyl-2-propynyl)-N-hydroxyurea, (R)-N-(3-(5-(2-quinolylmethyl)thien-2-yl)-1-methyl-2-propynyl)-N-hydroxyurea, N-(3-(5-(4-fluorophenylmethyl)thien-2-yl)-2-propynyl)-N-hydroxyurea, (R)-N-(3-(5-(4-fluorophenylmethyl)-3-chlorothien-2-yl)-1-methyl-2-propynyl)-N-hydroxyurea, (R)-N-(3-(5-(4-fluorophenoxymethyl)thien-2-yl)-1-methyl-2-propynyl)-N-hydroxyurea, (R)-N-(3-(5-(4-fluorophenylethyl)thien-2-yl)-1-methyl-2-propynyl)-N-hydroxyurea, (R)-N-(3-(5-(2-pyridylhydroxymethyl)thien-2-yl)-1-methyl-2-propynyl)-N-hydroxyurea, (R)-N-(3-(5-(4-fluorophenylmethoxymethyl)thien-2-yl)-1-methyl-2-propynyl)-N-hydroxyurea, (R)-N-(3-(5-(2-pyridylmethyl)thien-2-yl)-1-methyl-2-propynyl)-N-hydroxyurea, (R)-N-(3-(3-(4-fluorophenylmethyl)thien-2-yl)-1-methyl-2-propynyl)-N-hydroxyurea, (R)-N-(3-(4-(4-fluorophenylmethyl)thien-2-yl)-1-methyl-2-propynyl)-N-hydroxyurea, (R)-N-(3-(5-(pyrrolodin-2-one-1-methyl)thien-2-yl)-1-methyl-2-propynyl)-N-hydroxyurea, (R)-N-(3-(3,4-bis-(4-fluorophenylmethyl)thien-2-yl)-1-methyl-2-propynyl)-N-hydroxyurea, (R)-N-(3-(5-(4-fluorophenylmethyl)-5-methylthien-2-yl)-1-methyl-2-propynyl)-N-hydroxyurea, (R)-N-(3-(5-(4-biphenylhydroxymethyl)-5-methylthien-2-yl)-1-methyl-2-propynyl)-N-hydroxyurea, (R)-N-(3-(5-(4-biphenylmethyl)thien-2-yl)-1-methyl-2-propynyl)-N-hydroxyurea, (R)-N-(3-(5-(thiazo-4-ylmethyl)thien-2-yl)-1-methyl-2-propynyl)-N-hydroxyurea, (R)-N-(3-(5-(benzo(b)thien-2-ylhydroxymethyl)thien-2-yl)-1-methyl-2-propynyl)-N-hydroxyurea, (R)-N-(3-(5-(benzo(b)thien-2-ylmethyl)thien-2-yl)-1-methyl-2-propynyl)-N-hydroxyurea, (R)-N-(3-(3-(4-fluorophenylmethoxymethyl)thien-2-yl)-1-methyl-2-propynyl)-N-hydroxyurea, (R)-N-(3-(5-(2-(4-chlorophenyl)thiazo-4-ylmethyl)thien-2-yl)-1-methyl-2-propynyl)-N-hydroxyurea, (R)-N-(3-(5-(1,2-dihydro-1-methyl-2-oxoquinolin-6-ylmethoxymethyl)thien-2-yl)-1-methyl-2-propynyl)-N-hydroxyurea, (R)-N-(3-(5-(thiazo-2-ylmethyl)thien-2yl)-1-methyl-2-propynyl)-N-hydroxyurea, (R)-N-(3-(5-(4-fluorophenylmethyl)-2-bromothien-3-yl)-1-methyl-2-propynyl)-N-hydroxyurea, (R)-N-(3-(5-phenylmethylthien-2-yl)-1-methyl-2-propynyl)-N-hydroxyurea, and (R)-N-(3-(5-(4-fluorophenylcarbonyl-0-methyloxime)thien-2-yl)-1-methyl-2-propynyl)-N-hydroxyurea, Preferred compounds of this invention are those in which Z is optionally substituted thienyl.

Particularly preferred compounds of the present invention are (R,S)-N-{3-[5-(4-fluorophenylmethyl)thien-2-yl]-1-methyl-2-propynyl}-N-hydroxyurea; (R)-N-{3-[5-(4-fluorophenylmethyl)thien-2-yl]-1-methyl-2-propnyl}-N-hydroxyurea; and (S)-N-{3-[5-(4-fluorophenylmethyl)thien-2-yl]-1-methyl-2-propynyl}-N-hydroxyurea; with the R-enantiomer being most preferred.

Leukotriene Biosynthesis Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23187 challenge (final concentration of 8.3 µM) and the reaction terminated after 30 minutes by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis as illustrated in Table 1.

TABLE 1

In Vitro Inhibitory Potencies Against Stimulated $LTB_4$ Formation in Human Whole Blood

| Example | $IC_{50}$ (µM) or % inhibition |
|---|---|
| 1 | 0.06 |
| 2 | 72% @ 0.2 µM |
| 4 | 39% @ 0.8 µM |
| 5 | 0.62 |
| 6 | 40% @ 0.4 µM |
| 7 | 0.35 |
| 8 | 62% @ 0.2 µM |
| 9 | 0.3 |
| 12 | 0.07 |
| 13 | 0.07 |
| 15 | 0.93 |
| 19 | 0.13 |
| 21 | 0.23 |
| 22 | 51% @ 0.2 µM |
| 23 | 40% @ 0.2 µM |
| 24 | 0.56 |
| 25 | 84% @ 1.56 µM |
| 26 | 60% @ 0.78 µM |
| 27 | 46% @ 1.56 µM |
| 28 | 0.07 |
| 29 | 72% @ 0.2 µM |
| 30 | 0.16 |
| 31 | 0.14 |
| 32 | 57% @ 0.78 µM |
| 33 | 59% @ 0.2 µM |
| 34 | 33% @ 0.1 µM |
| 35 | 36% @ 0.1 µM |
| 36 | 44% @ 0.1 µM |
| 37 | 43% @ 0.78 µM |
| 38 | 33% @ 0.78 µM |
| 39 | 33% @ 0.2 µM |
| 40 | 63% @ 3.12 µM |
| 41 | 35% @ 0.78 µM |
| 42 | 3% @ 0.1 µM |
| 43 | 69% @ 1.56 µM |
| 44 | 86% @ 1.56 µM |
| 45 | 14% @ 0.1 µM |

TABLE 1-continued

In Vitro Inhibitory Potencies Against Stimulated $LTB_4$ Formation in Human Whole Blood

| Example | $IC_{50}$ (µM) or % inhibition |
|---|---|
| 46 | 4% @ 0.2 µM |
| 47 | 30% @ 0.78 µM |
| 48 | 73% @ 0.78 µM |
| 49 | 49% @ 0.1 µM |
| 50 | 43% @ 0.2 µM |
| 51 | 0.36 |

Inhibition of Leukotriene Biosynthesis in vivo

Inhibition of the biosynthesis of leuktrienes in vivo after oral administration of compound was determined using a rat peritoneal anaphylaxis model in a similar manner as that described by Young and coworkers (Young, P. R.; Dyer, R. D.; Carter, G. W., Fed. Proc., Fed. Am. Soc. Exp. Biol. 1985, 44: 1185). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. Compounds of this invention prevent the formation of leukotrienes in this model after oral administration in a range of 1–200 µmol/kg. Representative activity is shown in Table 2.

TABLE 2

In Vivo Inhibitory Potencies of Compounds of this Invention

| Example | $ED_{50}$ (mg/kg) or % inhibition |
|---|---|
| 1 | 68% @ 30 µmol/kg |
| 12 | 72% @ 30 µmol/kg |
| 19 | 38% @ 30 µmol/kg |
| 21 | 5.90 |
| 22 | 0.70 |
| 28 | 78% @ 30 µmol/kg |
| 30 | 41% @ 30 µmol/kg |
| 31 | 36% @ 30 µmol/kg |
| 33 | 56% @ 30 µmol/kg |
| 34 | 53% @ 30 µmol/kg |
| 48 | 36% @ 30 µmol/kg |
| 50 | 37% @ 30 µmol/kg |

Pharmaceutical Composition

The present invention also provides pharmaceutical compositions which comprise compounds of the present invention formulated together with one or more non-toxic pharmaceutically acceptable careers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracistemally, intravaginally, intraperitoneally, topically (as by powders, ointments, or drops), bucally, or as an oral or nasal spray. The term "parenteral" administration as used herein refers to modes of administration which include intravenous, intramuscular, intrapefitoneal, intrastemal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, partben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders. and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humechants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonitc clay, and i) lubricants such as talc, calcium stearate, magnesium stearate, solid polyethylene glycols, sodium lauryl surf ate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonitc, agar-agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at ambient temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilameliar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of this invention can be prepared by a variety of synthetic routes. Representative procedures are outlined as follows.

A general route to the compounds of this invention is shown in Scheme 1. Intermediate 3 (where Y is selected from >O, >S, and —CH=CH—) is prepared by a coupling 1a (where X is Br or Cl, and L is defined above) with 2a (where M is Li, Na, or Mg), or 1b with 2b. This reaction may be catalyzed by the addition of transition metal catalysts or their salts. The aryl moiety 3 is then converted to an aryl halide 4 which is coupled in the presence of catalyitic Pd(II) with alkynyl-N-hydroxyurea 5, to provide the desired product 6. Suitable palladium (II) catalysts include $Pd(OAc)_2$, $Pd(Ph_3P)_2Cl_2$, $Pd(CH_3CN)_2Cl_2$, and the like, preferably $Pd(CH_3CN)_2Cl_2$.

Scheme 1

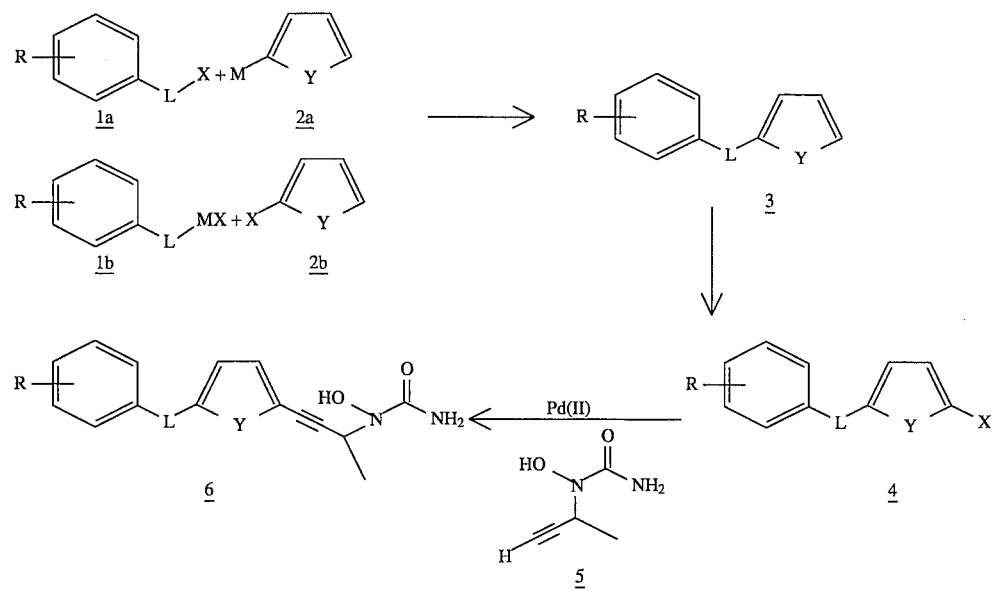

Scheme 2 illustrates an alternative route for the preparation of the compounds of this invention. The intermediate 8 is prepared by coupling 1a with 7 as described above. Hydrolysis of the diethyl acetal provides the aldehyde 9, which is oxidized to the intermediate carboxylic acid 10 (for example using $NaClO_2$ in DMSO and aqueous $NaH_2PO_4$). The carboxylic acid is converted into the iodo compound 11 using NaOH, $I_2$, and KI. Intermediate 11 is then coupled with alkynyl-N-hydroxyurea 5 as described above to provide 6.

Scheme 2

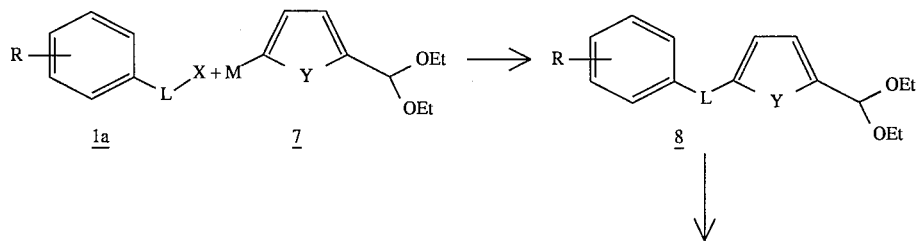

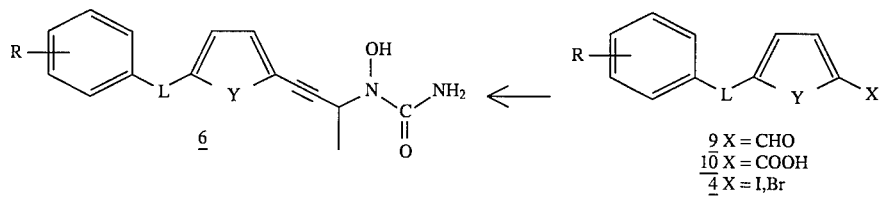

Another route to the compounds of this invention is shown in Scheme 3. Aryl halide 4 is convened to butynol 12 by Pd catalyzed coupling with 3-butyn-2-ol, or alternatively, aryl aldehyde 9 is converted to the substituted butynol 12 by treatment with carbon tetrabromide, triphenylphosphine and zinc, followed by lithium diisopropylamide and acetaldehyde. Reaction of butynol 12 with triphenylphosphine, diethyl azodicarboxylate and N,O-bis-phenoxycarbonylhydroxylamine according to the method of Stewart, A. O. and Brooks, D. W. *J. Org. Chem.* 1992, 57, 5020, gives 13. Treatment of 13 with ammonia or ammonium hydroxide provides the desired N-hydroxyurea.

synthetic sequence described in Reaction Schemes 3A and 3B. The process comprises the step of coupling 5-((4-fluorophenyl)methyl)-2-iodothiophene:

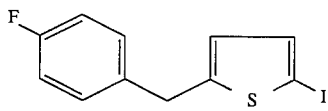

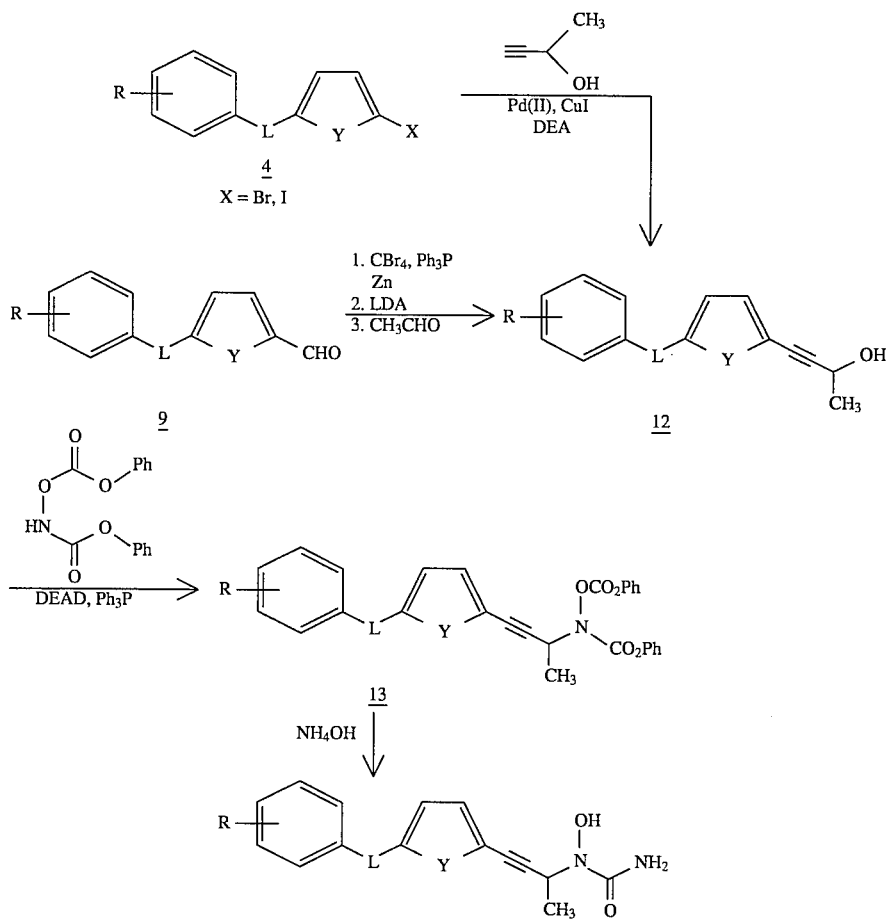

The most preferred compound of the present invention, (R)-N-{3-[5-(4-fluorophenylmethyl)thien-2-yl]-1-methyl-2-propynyl}-N-hydroxyurea, is best prepared by the general with an N-(3-butyn-2-yl)-N-hydroxyurea:

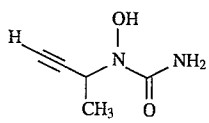

in the presence of a palladium coupling catalyst. In general, the process involves three distinct phases, including 1) the synthesis of the so-called "lefthand" (substituted phenylalkyl)thienyl iodide portion of the final product; 2) the synthesis of the so-called "righthand"N-hydroxyurea portion of the final product, and 3) coupling of the two precursor halves.

The lefthand (substituted phenyl)alkylthienyl precursor is synthesized by the reaction sequence depicted in Reaction Scheme 3A.

Reaction Scheme 3A

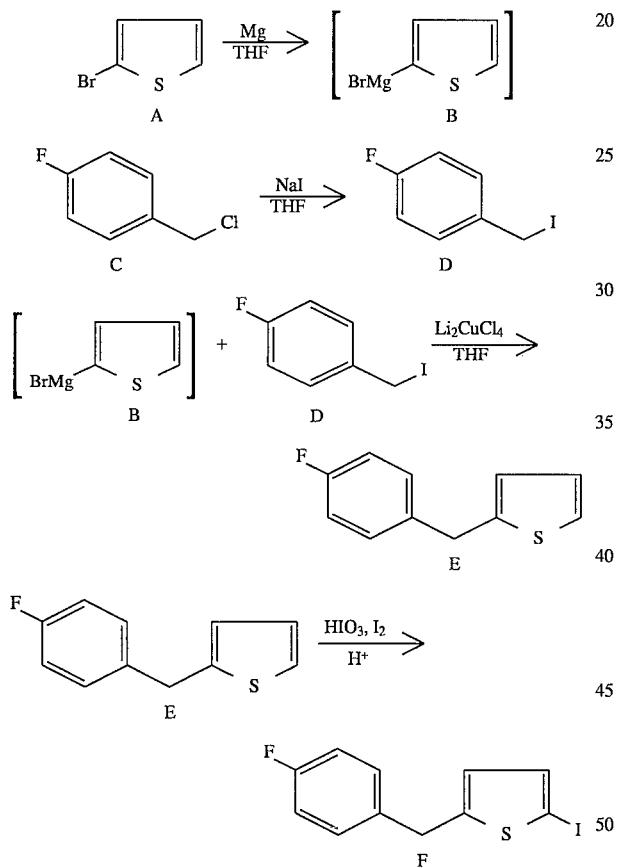

The commercially available 4-fluorobenzyl chloride, C, is converted to the corresponding 4-fluorobenzyl iodide, D, by reaction with sodium iodide in a suitable polar aprotic organic solvent such as tetrahydrofuran. Commercially available 2-bromothiophene, A, is converted under typical Grignard reaction conditions to the corresponding Grignard reagent, B.

The 4-fluorobenzyl iodide. D, is then reacted with the thiophenyl Grignard reagent in tetrahydrofuran in the presence of lithium tetrachlorocopper (II) which acts as a coupling catalyst to yield the desired 2-(4-fluorobenzylthiophene, E. 2-(4-Fluorobenzylthiophene, E, is then iodinated by the action of iodine in the presence of $HIO_3$ and sulfuric acid to produce the intermediate, 5-(4-fluorophenyl)methyl)-2-iodothiophene, F.

The righthand precursor portion of the end-product of the process of this invention is N-(3-butyn-2-yl)-N-hydroxyurea of the structure:

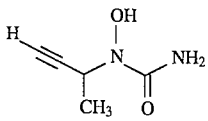

There is a chiral center in compounds of the structure shown immediately above at the carbon atom which bears the methyl substituent. The present invention contemplates process for making both enantiomers, as well as mixtures of the two including the racemic mixture.

The preferred method of synthesizing the righthand precursor is depicted in Reaction Scheme 6 below.

In the last step of the preferred method of making the preferred compound of this invention, the so-called "righthand" and "lefthand" portions of the molecule are coupled by the action of a palladium coupling catalyst and a copper salt such as copper (I) iodide in a suitable solvent in the presence of triphenylphosphine. The coupling reaction may be carried out in variety of solvents with equal success. Some examples of solvent are isopropyl acetate, DMF, $CH_3CN$, EtOAc, $CH_2Cl_2$, isopropyl acetate/water (biphasic), with isopropyl acetate being preferred. The preferred palladium coupling catalyst for this reaction is bis(acetonitrilo)palladium (II) chloride, $(CH_3CN)_2PdCl_2$. This catalyst generally produces the desired product in yields exceeding 80%. Suitable alternative palladium catalysts include $PdCl_2$, $PdOAc_2$, $Pd(PPh_3)_4$, and polymer supported Pd(O), but these catalysts gave product in 30–55% yield along with a cyclic byproduct.

Preparation of the enantiomers of N-hydroxy-N-(3-butyn-2-yl)urea 5 is shown in Schemes 4–6. Isolation of (R)-(+)-N-hydroxy-N-(3-butyn-2-yl)urea and (S)-(−)-N-hydroxy-N-(3-butyn-2-yl)urea by chiral derivitization and separation of the diastereomers is shown in Scheme 4. Reaction of 3-butyn-1-ol with N,O-bis(phenoxycarbonyl)hydroxylamine, triphenylphosphine, and diethylazodicarboxylate as described in Scheme 3 and treatment of the resulting N,O-bis(phenoxycarbonyl) derivative with $NH_4OH$ in methanol gives N-(1-butyn-3-yl)-N-hydroxyphenylcarbamate 14. Treatment of a solution of 14 in anhydrous $CH_2Cl_2$ with N-(9-fluorenylmethoxycarbonyl)-L-phenylalanine 15 and 1,3-dicyclohexylcarbodiimide followed by chromatography on silica gel (5% ether/toluene) gives diastereomers 16 (54%, S configuration at the stereocenter adjacent to the triple bond), and 17 (45%, R configuration at the stereocenter adjacent to the triple bond). (S)-(−)-N-hydroxy-N-(3-butyn-2-yl)urea 19 is obtained from 16 and (R)-(+)-N-hydroxy-N-(3-butyn-2-yl)urea 21 is obtained from 17 by cleavage of the chiral auxiliary with NH4OH in dioxane, followed by aminolysis with liquid ammonia.

Scheme 4

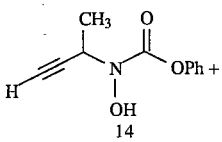

-continued
Scheme 4

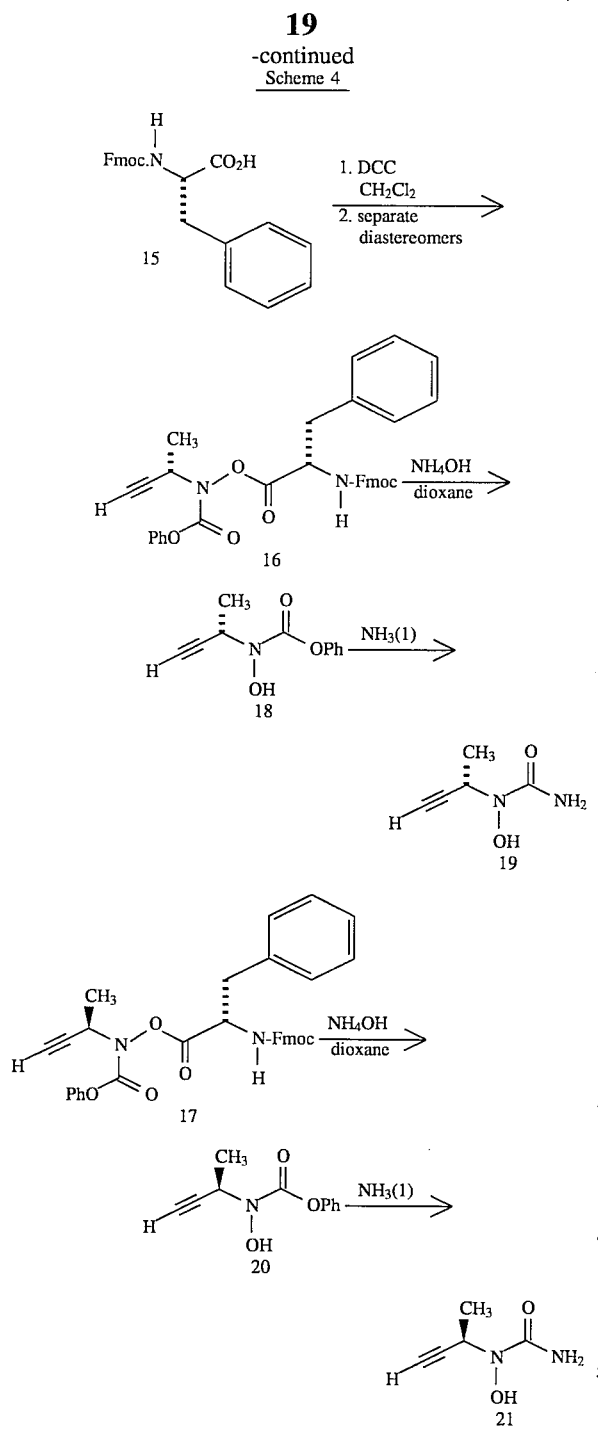

The preparation of (R)-(+)-N-hydroxy-N-(3-butyn-2-yl)urea and (S)-(−)-N-hydroxy-N-(3-butyn-2-yl)urea through chemical synthesis is shown in Scheme 5. Epoxidation of trans-crotyl alcohol with L-(+)-diisopropyltartrate, Titanium (IV) isopropoxide, and tert-butyl hydroperoxide followed by sulfonylation of the free OH to form (2S-trans)-oxiranemethanol derivative 22 is performed as described by Gao, Y, Hanson, R. M., Klunder, J. M., Soo, Y. K., Masamune, H, and Sharpless, K. B. *J. Am. Chem. Soc,* 1987, 109, 5765. Treatment of 22 with n-butyllithium in THF, at −70° to −60° C. produces alkynol 23. Coupling of 23 with N,O-diphenoxycarbonylhydroxylamine in the presence of triphenylphosphine and diethylazodicarboxylate proceeds with complete inversion of the chiral center to form 24.

Aminolysis with NH₃ provides the (R)-N-hydroxyurea 21. (S) acetylenic N-hydroxyurea 19 is obtained as described above, except substituting D-(−)-sopropyltartrate, for L-(+)-diisopropyltartrate, for L-(+)-diisopropyltartrate.

Scheme 5

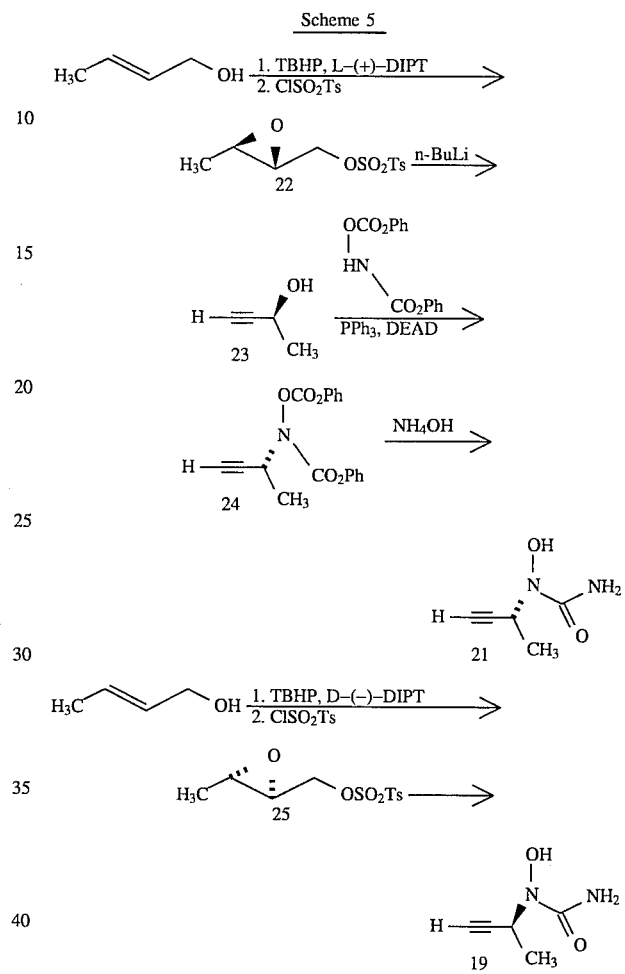

The preferred preparation of (R)-(+)-N-hydroxy-N-(3-butyn-2-yl)urea is outlined in Scheme 6. Treatment of (S)-3-butyn-2-ol 27 with RSO₂Cl and triethylamine produces sulfonate 28. Representative values for R include methyl, trifluoromethyl, phenyl, p-tolyl, 1,3,5-trimethoxyphenyl, and the like, preferably p-tolyl. Reaction of 28 with hydroxylamine in alcohol (for example methanol, ethanol, isopropanol, and the like), preferably 55% aqueous hydroxylamine in methanol, gives 29, which is converted to (R)-N-hydroxy-N-(3-butyn-2-yl)urea 21 by treatment with cyanate ion, preferably KOCN.

Scheme 6

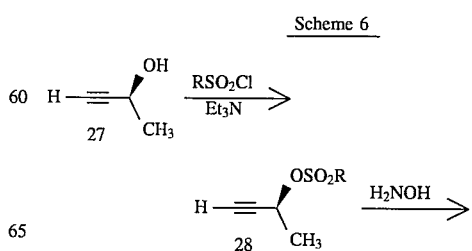

-continued
Scheme 6

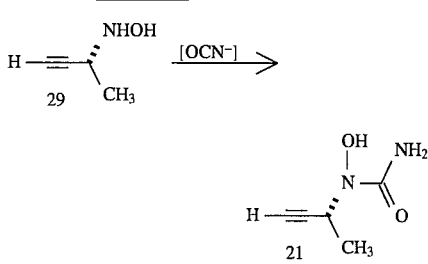

The foregoing may be better understood by reference to the following examples which are provided for illustration and not intended to limit the scope of the inventive concept. The following abbreviations are used: THF for tetrahydrofuran, n-BuLi for n-butyllithium, DMF for N,N-dimethylformamide, $CDCl_3$ for deuterochloroform, DMSO-$d_6$ for deuterodimethylsulfoxide, DIBALH (diisobutylaluminum hydride) for diisobutylahminum hydride, LAH for lithium aluminum hydride, LDA for lithium diisopropylamide and TDA-1 for tris[2-(2-methoxyethoxy)ethyl]amine.

EXAMPLE 1

Preparation of N-{3-[5-(4-fluorophenylmethyl)fur-2-yl]-1-methyl-2-propynyl}-N-hydroxyurea.
Step 1. 2-(4-fluorophenylmethyl)furan.

To a 0° C. solution of furan (13.6 g, 0.20 mol) in a mixture of anhydrous ether (230 mL) and anhydrous THF (70 mL) under nitrogen was added a 2.5M solution of n-butyllithium in hexane (54.0 mL, 0.134 mol). The mixture was stirred at 0° C. for 1.5 hours and then transferred by cannula to a stirred −78° C. solution of 4-fluorobenzyl bromide (23.6 g, 0.125 mol) and tetrakis-(triphenylphosphine)palladium (O) (1.25 g, 0.001 mol) in anhydrous THF (200 mL). The transfer was made under nitrogen over a period of 30–40 minutes. The reaction mixture was stirred at ambient temperature overnight, saturated aqueous solution of ammonium chloride was added and the mixture extracted with ether. The ether layer was dried ($MgSO_4$), concentrated in vacuo and the residue distilled at reduced pressure to give 2-(4-fluorophenylmethyl)furan as a colorless oil (17.89 g, 81%). b.p. 57°–62° C. at 0.5–0.7 mm-Hg.
Step 2. 2-Bromo-5-(4-fluorophenylmethyl)furan.

To a −30° C. solution of 2-(4-fluorophenylmethyl)furan, prepared as in step 1 (32.0 g, 0.18 mol) in anhydrous DMF (60 mL) was added a solution of bromine (28.9 g, 0.18 mol) in $CH_2Cl_2$ (250 mL). The mixture was stirred for 0.5 hours at −10° C. and poured into pentane (1600 mL). The penlane was then decanted from the dark colored insoluble layer. Evaporation of the pentane gave the crude product which was purified by flash-chromatography on silica gel eluting with penlane to provide 2-Bromo-5-(4-fluorophenylmethyl) furan as a cream colored solid in a yield of 8.87 g (19.2%).
Step 3. 4-(5-{4-fluorophenylmethyl}fur-2-yl)-3-butyn-2-ol.

A solution of 2-bromo-5-(4-fluorophenylmethyl)furan, prepared as in step 2, (23.65 g, 92.7 mmol) and D,L-3-butyn-2-ol (8.19 g, 117 mmol) in piperidine (125 mL) was stirred and treated with tetrakis (triphenylphosphine) palladium (0) (0.34 g), copper (I) iodide (0.22 g) and triphenylphosphine (0.22 g). The mixture was stirred under nitrogen and heated to reflux for 1.5 hours, cooled and treated with ice, saturated $NH_4Cl$ solution (300 mL) and 3N HCl (300 mL). The mixture was shaken and extracted with $CH_2Cl_2$ (2×400 mL). The combined organic layers were washed with additional 3N HCl until the washes were acidic, dried ($MgSO_4$) and concentrated in vacuo. The resulting residue was purified by flash chromatography on silica eluting with $CH_2Cl_2$ to afford 17.0 g (75%) of 4-(5-{4-Fluorophenylmethyl}fur-2-yl)-3-butyn-2-ol.
Step 4. N,O-bisphenoxycarbonyl-N-4-(5-{4-fluorophenylmethyl}fur-2-yl)-1-methyl-2-propynyl]hydroxylamine.

To a stirred 0° C. solution of 4-(5-{4-fluorophenylmethyl}fur-2-yl)-3-butyn-2-ol, prepared as in step 3 (9.37 g, 38.3 mmol),N,O-bis-phenyloxycarbonylhydroxylamine (12.6 g, 46.1 mmol), prepared according to the method of Stewart, A. O. and Brooks, D. W. *J. Org. Chem.* 1992, 57,5020, and triphenylphosphine (13.1 g, 49.9 mmol) in anhydrous THF (800 mL) was added a solution of diisopropyl azodicarboxylate (10.1 g, 49.9 mmol) in anhydrous THF (400 mL) dropwise. The reaction mixture was allowed to warm to ambient temperature, concentrated in vacuo at 45° C. and the residue treated with a 1:1 mixture of etherpenlane (400 mL) and stored overnight at −20° C. The ether-pentane solution was decanted from the solids which had separated and concentrated again in vacuo to a residue which upon purification by flash-chromatography on silica gel eluting with 2:1 $CH_2Cl_2$-pentane afforded 7.55 g (39%) of N,O-bisphenoxycarbonyl-N-4-(5-{4-fluorophenylmethyl}fur-2-yl)-1-methyl-2-propynyl]hydroxylamine.
Step 5. N-{3-[5-(4-fluorophenylmethyl)fur-2-yl]-1-methyl-2-propynyl}-N-hydroxyurea.

A solution of N,O-bisphenoxycarbonyl-N-4-(5-{4-fluorophenylmethyl}fur-2-yl)-1-methyl-2-propynyl]hydroxylamine, prepared as in step 4, (13.53 g, 27.0 mmol) in methanol (450 mL) was treated with concentrated aqueous ammonium hydroxide (150 mL) and the mixture stirred while stoppered overnight at ambient temperature. The reaction mixture was concentrated in vacuo and the residue purified by flash chromatography on silica eluting with 7% $CH_3OH$—$CH_2Cl_2$. The fractions containing the product were combined, concentrated in vacuo and the residue triturated with $CH_2Cl_2$ to give 4.22 g (52%) of N-{3-[5-(4-fluorophenylmethyl)fur-2-yl]-1-menthyl-2-propynyl}-N-hydroxyurea as a white solid. m.p. 154.5°–155.5° C. $^1H$ NMR (DMSO-$d_6$, 300 MHz) δ1.33 (d, J=6 Hz, 3H), 3.96 (s, 2H), 5.12 (q, J=6 Hz, 1H), 6.19 (d, J=3 Hz, 1H), 6.52 (s, 2H), 6.61 (d, J=3 Hz, 1H), 7.10–7.17 (m, 2H), 7.22–7.30 (m, 2H), 9.33 (s, 1H). MS (DCI/$NH_3$) m/e 303 (M+H)$^+$, 320 (M+$NH_4$)$^+$. Anal calcd for $C_{16}H_{15}FN_2O_3$: C, 63.57; H, 5.00; N, 9.27. Found: C, 63.32; H, 5.01; N, 9.14.

EXAMPLE 2

Preparation of N-[3-(5-{4-fluorophenylacetyl}fur-2-yl)-1-methyl-2-propynyl]-N-hydroxyurea.

The title compound was prepared according to the procedures described in Example 1 except substituting 4-fluorobenzoyl chloride for 4-fluorobenzylbromide. m.p. 154.5°–156° C. $^1H$ NMR (DMSO-$d_6$, 300 MHz) δ1.40 (d, J=6 Hz, 3H), 5.21 (q, J=6 Hz, 1H), 6.60 (s, 2H), 7.01 (d, J=3 Hz, 1H), 7.36–7.46 (m, 3H), 7.95–8.03 (m, 2H), 9.47 (s, 1H). IR (KBR) 3420, 1730, 1595, 1490 cm$^{-1}$. MS (DCI/$NH_3$) m/e 317 (M+H)$^+$, 334 (M+$NH_4$)$^+$. Anal calcd for $C_{16}H_{13}FN_2O_4$: C, 60.67; H, 4.14; N, 8.86. Found: C, 60.81; H, 4.08; N, 8.81.

EXAMPLE 3

Preparation of N-[3-(5-{2-phenylethynyl}thien-2-yl)-1-methyl-2-propynyl]-N-hydroxyurea.

The title compound was prepared according to the procedures described in Example 1 except substituting 2-bromo-5-{2-phenylethynyl}thiophene for 2-bromo-5-(4-fluorophenylmethyl)furan. $^1$H NMR (DMSO-$d_6$, 300 MHz) δ1.46 (d, J=6 Hz, 3H), 5.17 (q, J=6 Hz, 1H), 6.58 (bs, 2H), 7.25 (d, J=3 Hz, 1H), 7.35 (d, J=3 Hz, 1H), 7.45 (m, 3H), 7.57 (m, 2H), 9.41 (s, 1H). MS (DCI/NH$_3$) m/e 311 (M+H)$^+$, 328 (M+NH$_4$)$^+$. Anal calcd for $C_{17}H_{14}N_2O_4S$: C, 65.80; H, 4.51; N, 9.03. Found: C, 65.35; H, 4.53; N, 8.92.

EXAMPLE 4

Preparation of N-[3-(5-{2-[3-pyridyl]ethenyl}fur-2-yl)-1-methyl-2-propynyl]-N-hydroxyurea.

Step 1. N,O-bis(phenoxycarbonyl)-N-(3-butyn-2-yl)hydroxylamine.

To a 0° C. solution in THF (200 mL) of 3-butyn-2-ol (3.00 g, 42.9 mmol), N,O-bis(phenoxycarbonyl)hydroxylamine (11.7 g, 42.9 mmol), and triphenylphosphine (11.7 g, 42.9 mmol), was added dropwise diethylazodicarboxylate (7.40 g, 42.8 mmol). The reaction mixture was stirred for 2 hours at 0°–5° C. and then was concentrated almost to dryness. The residue was diluted with ethyl acetate, the solids were filtered off, and the flitrate was concentrated in vacuo. Chromatography on silica gel (5% ethyl acetate, pentane) provided N,O-bis(phenoxycarbonyl)-N-(3-butyn-2-yl)hydroxylamine (12.3 g, 88% ).

Step 2. N-hydroxy-N-(3-butyn-2-yl)urea.

A mixture of N,O-Bis(phenoxycarbonyl)-N-(3-butyn-2-yl)hydroxylamine (3.14 g,9.7 mmol), methanol (20 mL), and ammonium hydroxide (20 mL) was stirred for 17 hours at ambient temperature. The reaction mixture was concentrated in vacuo and the residue was dissolved in ethyl acetate. The organic solution was washed with brine, dried over MgSO$_4$, filtered, and concentrated. Chromatography on silica gel (2% methanol, methylene chloride) afforded N-hydroxy-N-(3-butyn-2-yl)urea (340 mg, 28%). $^1$H NMR (DMSO-26, 300 MHz) δ1.25 (d, 3H, J=7.5 Hz), 3.05 (d, 1H, J=3.0 Hz), 4.85 (dq, 1H, J=7.5, 3.0 Hz), 6.50 (br s, 1H), 9.25 (s, 1H). MS (DCI/NH$_3$) m/e 129 (M+H)$^+$, 146 (M+NH$_4$)$^+$. Anal calcd for $C_5H_8N_2O_2$: C, 46.87; H, 6.29; N, 21.86. Found: C, 47.03; H, 6.27; N, 21.98.

Step 3. Diethyl 3-pyridylmethylphosphonate.

To a stirred solution of saturated NaHCO$_3$ was added 3-picolyl chloride hydrochloride (8.2 g, 50 mmol). After gas evolution ended, the mixture was extracted with CH$_2$Cl$_2$. The organic phase was dried (MgSO$_4$) and concentrated in vacuo. To the resulting residue was added triethylphosphite (8.3 g, 50 mmol) and the neat mixture was stirred and heated at 85° C. overnight. The mixture was cooled and purified by flash column chromotography on silica gel eluting with 5% MeOH—CH$_2$Cl$_2$ to afford 3.0 g of diethyl 3-pyridylmethylphosphonate as a yellow oil.

Step 4. 2-[2-{3-pyridyl}ethenyl]furan.

To a stirred −78° C. solution of diethyl 3-pyridylmethylphosphonate (3.0 g, 13 mmol), prepared as in step 3, in THF (50 mL) was added n-butyllithium (25 mL, 55 mmol, 2.5M in hexanes). The cold reaction mixture was stirred 0.5 hours followed by the slow addition of furfuraldehyde (1.24 g, 13 mmol). The reaction was stirred 2 hours at −78° C. and the ice bath removed and allowed to stir at ambient temperature overnight. Saturated NH$_4$Cl was added and the mixture was diluted with ether. The organic layer was washed with brine, dried (MgSO$_4$) and concentrated in vacuo. The resulting residue was purified by column chromatography on silica gel eluting with 40% ethyl acetate-hexanes to afford 1.1 g of 2-[2-{3-pyridyl}ethenyl]furan.

Step 5. 2-iodo-5-[2-{3-pyridyl}ethenyl]furan.

To a stirred −78° C. solution of 2-[2-{3-pyridyl}ethenyl] furan (0.95 g, 5.5 mmol), prepared as in step 4, in THF (25 mL) was added lithium diisopropylamide (4 mL, 6 mmol, 1.5M in hexanes). The cold reaction mixture was stirred 1 hour, followed by the addition of a THF (3 mL) solution of iodine (1.39 g, 5.5 mmol). The ice bath was removed and the reaction mixture allowed to stir at ambient temperature overnight. Saturated NH$_4$Cl was added and the mixture diluted with ether. The organic layer was washed with brine, dried (MgSO$_4$) and concentrated in vacuo. The resulting residue was purified by column chromatography on silica gel eluting with 40% ethyl acetate-hexanes to afford 1.1 g of 2-iodo-5-[2-{3-pyridyl}ethenyl]furan.

Step 6. N-[3-(5-{2-[3-pyridyl]ethenyl}fur-2-yl)-1-methyl-2-propynyl]-N-hydroxyurea.

To a stirred solution of 2-iodo-5-[2-{3-pyridyl}ethenyl] furan (1.4 g, 4.7 mmol), prepared as in step 5, and N-hydroxy-N-(butyn-2-yl)urea (0.64 g, 5 mmol), prepared as in step 2, in diethylamine (10 mL) was added dimethylformamide (1 mL), triphenylphosphine (0.026 g, 0.1 mmol), cuprous iodide (5 mg, 25 mmol) and bis(acetonitrile)palladium(II) chloride (13 mg, 50 mmol). The mixture was stirred overnight at ambient temperature. Aqueous NH$_4$OH was added and the mixture extracted thoroughly with CH$_2$Cl$_2$. The combined organic layer was washed with brine, dried (MgSO$_4$) and evaporated under reduced pressure. The resulting residue was purified by column chromatography on silica gel eluting with 5% MeOH—CH$_2$Cl$_2$ to afford an off-white solid. Recrystallization from ethyl acetate-hexanes gave 530 mg of the title compound. m.p. 166° C. $^1$H NMR (DMSO-$d_6$, 300 MHz) δ1.38 (d, J=7 Hz, 3H), 5.19 (q, J=7 Hz, 1H), 6.61 (bs, 2H), 6.82 (d, J=3 Hz, 1H), 6.82 (d, J=3 Hz, 1H), 7.09 (d, J=16 Hz, 1H), 7.25 (d, J=16 Hz, 1H), 7.39 (m, 1H), 7.77 (m, 1H), 8.03 (m, 1H), 8.45 (m, 1H), 8.77 (m, 1H), 9.43 (s, 1H). MS (DCI/NH$_3$) m/e 298 (M+H)$^+$. Anal calcd for $C_{16}H_{15}N_3O_3$: C, 64.63; H, 5.08; N, 14.13. Found: C, 64.01; H, 5.09; N, 14.06.

EXAMPLE 5

Preparation of N-[3-(5-{2-[4-fluorophenyl]ethenyl}fur-2-yl)-1-methyl-2-propynyl]-N-hydroxyurea The title compound was prepared following the procedures described in Example 4 except substituting 4-fluorobenzylbromide for 3-picolyl chloride hydrochloride. m.p. 177° C. $^1$H NMR (DMSO-$d_6$, 300 MHz) δ1.38 (d, J=7 Hz, 3H), 5.18 (q, J=7 Hz, 1H), 6.56 (d, J=3 Hz, 1H), 6.60 (bs, 2H), 6.80 (d, J=3 Hz, 1H), 7.07 (s, 2H), 7.20 (m, 2H), 7.65 (m, 2H), 9.42 (s, 1H). MS (DCI/NH$_3$) m/e 315 (M+H)$^+$, 332 (M+NH$_4$)$^+$. Anal calcd for $C_{17}H_{15}FN_2O_3$: C, 64.95; H, 4.81; N, 8.91. Found: C, 64.44; H, 4.85; N, 8.85.

EXAMPLE 6

Preparation of N-[3-(5-{2-phenylethenyl}fur-2-yl)-1-methyl-2-propynyl]-N-hydroxyurea.

The title compound was prepared following the procedures described in Example 4 except substituting benzylbromide for 3-picolyl chloride hydrochloride. m.p. 168° C. $^1$H NMR (DMSO-$d_6$, 300 MHz) δ1.38 (d, J=7 Hz, 3H), 5.19 (q, J=7 Hz, 1H), 6.59 (m, 3H), 6.80 (d, J=3 Hz, 1H), 7.08 (m, 2H), 7.24–7.42 (m, 3H), 7.59 (m, 2H), 9.42 (s, 1H). MS (DCI/NH$_3$) m/e 297 (M+H)$^+$, 314 (M+NH$_4$)$^+$. Anal calcd for $C_{17}H_{16}N_2O_3$: C, 68.90; H, 5.44; N, 9.45. Found: C, 68.53; H, 5.47; N, 9.42.

EXAMPLE 7

Preparation of N-[3-(5-{2-[2-pyridyl]ethenyl}fur-2-yl)-1-methyl-2-propynyl]-N-hydroxyurea.

The title compound was prepared following the procedures described in Example 4 except substituting 2-picolyl chloride hydrochloride for 3-picolyl chloride hydrochloride. m.p. 175° C. $^1$H NMR (DMSO-d$_6$, 300 MHz) δ1.39 (d, J=7 Hz, 3H), 5.19 (q, J=7 Hz, 1H), 6.61 (bs, 2H), 6.74 (d, J=3 Hz, 1H), 6.82 (d, J=3 Hz, 1H), 7.12 (d, J=16 Hz, 1H), 7.25 (m, 1H), 7.48 (d, J=16 Hz, 1H), 7.54 (d, J=7 Hz, 1H), 7.77 (m, 1H), 8.56 (m, 1H), 9.43 (s, 1H). MS (DCI/NH$_3$) m/e 298 (M+H)$^+$. Anal calcd for $C_{16}H_{15}N_3O_3$: C, 64.63; H, 5.08; N, 14.13. Found: C, 64.52; H, 4.84; N, 14.07.

EXAMPLE 8

Preparation of N-[3-(5-{2-[4-Fluorophenyl]ethenyl}thien-2-yl)-1-methyl-2-propynyl]-N-hydroxyurea.

The title compound was prepared following the procedures described in Example 4 except substituting 4-fluorobenzylbromide for 3-picolyl chloride hydrochloride and substituting thiophene-2-carboxaldehyde for furfuraldehyde. m.p. 177° C. $^1$H NMR (DMSO-d$_6$, 300 MHz) δ1.37 (d, J=7 Hz, 3H), 5.17 (q, J=7 Hz, 1H), 6.58 (bs, 2H), 6.98 (d, J=16 Hz, 1H), 7.10–7.26 (m, 4H), 7.37 (d, J=16 Hz, 1H), 7.63 (m, 2H), 9.39 (s, 1H). MS (DCI/NH$_3$) m/e 331 (M+H)$^+$, 348 (M+NH$_4$)$^+$. Anal calcd for $C_{17}H_{15}FN_2O_2S$: C, 61.81; H, 4.57; N, 8.48. Found: C, 61.61; H, 4.59; N, 8.47.

EXAMPLE 9

Preparation of N-[3-(5-{2-[4-methylphenyl]ethenyl}fur-2-yl)-1-methyl-2-propynyl]-N-hydroxyurea.

The title compound was prepared following the procedures described in Example 4 except substituting 4-methylbenzylbromide for 3-picolyl chloride hydrochloride. m.p. 174° C. $^1$H NMR (D$_3$COD, 300 MHz) δ1.50 (d, J=7 Hz, 3H), 2.33 (s, 3H), 5.26 (q, J=7 Hz, 1H), 6.38 (d, J=3 Hz, 1H), 6.60 (d, J=3 Hz, 1H), 6.87 (d, J=16 Hz, 1H), 7.03 (d, J=16 Hz, 1H), 7.15 (m, 2H), 7.38 (m, 2H). MS (DCI/NH$_3$) m/e 311 (M+H)$^+$, 328 (M+NH$_4$)$^+$. Anal calcd for $C_{18}H_{18}N_2O_3$: C, 69.65; H, 5.84; N, 9.02. Found: C, 69.50; H, 5.74; N, 8.96.

EXAMPLE 10

Preparation of N-{3-[3-(O-benzyloxycarboxaldoxime)phenyl]-3-butyn-2-y}]-N-hydroxyurea.
Step 1. 3-bromobenzaldehyde diethyl acetal.

To a stirred solution of 3-bromobenzaldehyde (22.38 g, 121 mmol) in ethanol (150 mL) was added triethylonhoformate (27 g, 181 mmol) and concentrated HCl (0.5 mL). The mixture was heated to reflux for 3 hours and allowed to cool to ambient temperature. The reaction mixture was poured into ice/H$_2$O and extracted thoroughly with hexanes. The combined organic extracts were washed with water and brine, dried (MgSO$_4$) and concentrated in vacuo to give 34 g of 3-bromobenzaldehyde diethyl acetal as a colorless liquid.
Step 2. 3-iodobenzaldehyde diethyl acetal.

To a stirred −78° C. solution of 3-bromobenzaldehyde diethyl acetal, prepared as in step 1, (1.0 g, 3.8 mmol) in THF (10 mL) was added n-butyllithium (1.7 mL, 4.25 mmol, 2.5M in hexanes). The cold reaction mixture was stirred 0.5 hours followed by the addition of a THF (5 mL) solution of iodine (1.09 g, 4.25 mmol). The ice bath was removed and the reaction allowed to warm to ambient temperature. Saturated NH$_4$Cl was added and the mixture diluted with hexanes. The organic layer was washed with brine, dried (MgSO$_4$) and concentrated under reduced pressure to give a residue which was purified by column chromatography on silica gel eluting with 5% ethyl acetate-hexanes to afford 1.0 g of 3-iodobenzaldehyde diethyl acetal.
Step 3. N-{3-[3-(carboxaldehyde diethyl acetal)phenyl]-1-methyl-2-propynyl}-N-hydroxyurea.

To a stirred solution of 3-iodobenzaldehyde diethyl acetal (1.0 g, 3.28 mmol), prepared as in step 2, and N-hydroxy-N-(butyn-2-yl)urea (0.42 g, 3.28 mmol), prepared as in Example 4, steps 1 and 2, in diethylamine (5 mL) was added dimethylformamide (0.5 mL), triphenylphosphine (84 mg, 0.32 mmol), cuprous iodide (0.30 mg, 0.16 mmol) and bis(acetonitrile)palladium(II) chloride (115 mg, 0.16 mmol). The mixture was stirred overnight at ambient temperature and aqueous NH$_4$OH was added. The mixture was extracted thoroughly with ethyl acetate and the combined organic extracts were washed with brine, dried (MgSO$_4$) and evaporated under reduced pressure. The residue was purified by column chromatography on silica gel eluting with 7% MeOH-CH$_2$Cl$_2$ to afford 0.34 g of N-{3-[3-(carboxaldehyde diethyl acetal)phenyl]-1-methyl-2-propynyl}-N-hydroxyurea.
Step 4. N-{3-[3-(O-benzyloxycarboxaldoxime)phenyl]-1-methyl-2-propynyl}-N-hydroxyurea.

N-{4-[3-(carboxaldehyde diethyl acetal)phenyl]-1-methyl-2-propynyl}-N-hydroxyurea (0.26 g, 0.85 mmol), prepared as in step 3, was dissolved in ethanol (8 mL) and water (2 mL). To this stirred solution was added O-benzylhydroxylamine hydrochloride (0.27 g, 1.7 mmol). The mixture was stirred 2 hours at ambient temperature and poured into water. The mixture was extracted thoroughly with ethyl acetate and the combined organic extracts washed with water and brine, dried (MgSO$_4$), filtered and concentrated in vacuo to give a thick oil that solidified upon standing. Recrystalization from ethyl acetate-hexanes afforded 0.21 g of N-{3-[3-(O-benzyloxycarboxaldoxime)phenyl]-1-methyl-2-propynyl}-N-hydroxyurea. m.p. 146°–148° C.(dec). $^1$H NMR (DMSO-d$_6$, 300 MHz) δ1.36 (d, J=6 Hz, 3H), 5.13 (q, J=6 Hz, 1H), 5.18 (s, 2H), 6.57 (bs, 2H), 7.29–7.47 (m, 7H), 7.57–7.65 (m, 2H), 9.36 (s, 1H). MS (DCI/NH$_3$) m/e 355 (M+H)$^+$.

EXAMPLE 11

Preparation of N-{3-[(3-phenylcarbonyl)phenyl]-1-methyl-2-propynyl}-N-hydroxyurea.

The title compound is prepared following the procedures described in Example 1 except substituting N-methoxy-N-methyl-3-bromobenzamide for 4-fluorobenzylbromide and phenylmagnesiumbromide for lithiofuran.

EXAMPLE 12

Preparation of N-{3-[5-(4-fluorophenylmethyl)thien-2-yl]-1-methyl-2-propynyl}-N-hydroxyurea.
Step 1. 2-(4-fluorophenylmethyl)thiophene.

A solution of thiophene (12.6 g, 0.15 mol) in a mixture of anhydrous ether (230 mL) and anhydrous THF (70 mL) was treated dropwise at 0° C. with a 2.5M solution of n-butyllithium in hexane (54.0 mL, 0.134 mol). The mixture was stirred at 0° C. for 1.5 hours and then transferred by cannula into a −78° C. solution of 4-fluorobenzyl bromide (23.6 g, 0.125 mol) containing tetrakis(triphenylphosphine) palladium(0) (1.25 g) in anhydrous THF (200 mL). The reaction mixture was stirred at ambient temperature under nitrogen overnight and then quenched with saturated NH₄Cl solution (100 mL) and partitioned between ether and additional NH₄Cl solution. The ether layer was dried over MgSO₄, concentrated in vacuo and the residue subjected to vacuum distillation to give 19.4 g (81%) of 2-(4-fluorophenylmethyl)thiophene. b.p. 74°–83° C. at 0.6–0.7 mm of Hg.

Step 2. 2-bromo-5-(4-fluorophenylmethyl)thiophene.

Bromination of 2-(4-fluorophenylmethyl)thiophene (9.61 g, 50.0 mmol), prepared as in step 1, with N-bromosuccinimide (8.90 g, 50.0 mmol) in CHCl₃ and CH₃COOH (1:1) provided 13.3 g (98%) of 2-bromo-5-(4-fluorophenylmethyl)thiophene.

Step 3. 4-[5-(4-fluorophenylmethyl)thien-2-yl]-3-butyn-2-ol

4-[5-(4-fluorophenylmethyl)-2-thienyl]-3-butyn-2-ol (9.16 g, 71%) was prepared according to the method of Example 1, step 3, except substituting 2-bromo-5-(4-fluorophenylmethyl)thiophene (13.3 g, 49.0 mmol), prepared as in step 2, for 2-bromo-5-(4-fluorophenylmethyl)furan.

Step 4. N-{3-[5-(4-fluorophenylmethyl)thien-2-yl]-1-methyl-2-propynyl}-N-hydroxyurea.

N-{3-[5-(4-fluorophenylmethyl)thien-2-yl]-1-methyl-2-propynyl}-N-hydroxyurea was prepared in 33% yield according to the method of Example 1, step 4, except substituting 4-[5-(4-fluorophenylmethyl)thien-2-yl]-3-butyn-2-ol, prepared as in step 3, for 4-[5-(4-fluorophenylmethyl)fur-2-yl]-3-butyn-2-ol. m.p. 141°–142° C.(dec.). $^1$H NMR (DMSO-d₆, 300 MHz) δ1.32 (d, J=6.0 Hz, 3H), 4.10 (s, 2H), 5.10 (q, J=6.0 Hz, 1H), 6.50 (s, 2H), 6.80 (d, J=3.0 Hz, 1H), 7.05 (d, J=3.0 Hz, 1H),7.13 (m, 2H), 7.28 (m, 2H), 9.30 (s, 1H). MS (DCI/NH₃) m/e 319(M+H)⁺, 336 (M+H+NH₃)⁺. Anal calcd for C₁₆H₁₅FN₂O₂S: C, 60.36; H, 4.75; N, 8.80. Found: C, 60.53; H, 4.68; N, 8.80.

EXAMPLE 13

Preparation of (R)-N-{3-[5-(4-fluorophenylmethyl)thien-2-yl]-1-methyl-2-propynyl}-N-hydroxyurea.

Step 1. 2-(4-fluorophenylmethyl)thiophene.

To a 500-mL, three-necked flask equipped with a mechanical stirrer, pressure equalizing addition funnel, and a reflux condenser with N₂ inlet/outlet was added magnesium turnings (14.2 g, 0.58 g atom). The magnesium was dried with a heat gun under a stream of N₂, after which the flask was cooled to ambient temperature, the N₂ flow was reduced, and 200 mL on anhydrous diethyl ether was added. A solution of 4-fluorobenzyl chloride (73 g, 0.50 mol) in diethyl ether (50 mL) was prepared in the addition funnel. A few crystals of iodine and 5 mL of the solution were added to the reaction flask and reaction started instantaneously. The remaining solution was added dropwise over one hour, and the reaction mixture was then stirred at reflux for 30 min. In a separate flask a solution of dichloro [1,3-bis(diphenylphosphino)propane]nickel(II) (0.25 g, 0.50 mmol), and 2-bromothiophene (82 g, 0.50 mol) in diethyl ether (150 mL) was prepared and cooled in an ice bath. The grignard reagent was added over 10 min and the resulting clear tan solution was warmed slowly to ambient temperature. A mild exotherm occurred after one hour, after which the reaction was stirred for an additional hour at ambient temperature. The reaction mixture was diluted with 250 mL of diethyl ether and refluxed for 14 hours, then was cooled in an ice bath and cautiously quenched with 2N aqueous HCl (250 mL). The layers were separated and the aqueous phase was extracted twice with ether. The combined organic layers were washed with H₂O, saturated aqueous NaHCO₃, and H₂O, dried over MgSO₄, filtered, and concentrated in vacuo to give 93 g (97% yield) of 2-(4-fluorophenylmethyl)thiophene which was used without further purification.

Step 2. 2-iodo-5-(4-fluorophenylmethyl)thiophene.

A mixture of 2-(4-fluorophenylmethyl)thiophene (15 g, 78 mmol), prepared as in step 1, HIO₃ (2.8 g, 16 mmol), I₂ (7.9 g, 1.2 mmol), acetic acid (36 mL), concentrated sulfuric acid (1.2 mL), and H₂O (9 mL) was heated at 40° C. for 2 hours at which point all starting material was consumed by GC analysis. The reaction mixture was cooled to ambient temperature and H₂O (150 mL) and isopropyl acetate (150 mL) were added. The aqueous layer was separated, neutralized with saturated aqueous K₂CO₃, and extracted with isopropyl acetate (100 mL). The organic layers were combined and washed with H₂O (100 mL), saturated aqueous NaHCO₃ (2×100 mL), and saturated aqueous Na₂S₂O₃ (2×100 mL). The organic phase was then treated with activated carbon, dried over MgSO₄, filtered, and concentrated in vacuo to give a quantitative yield of 2-iodo-5-(4-fluorophenylmethyl)thiophene as a solution in isopropyl acetate, which is used without further purification.

Step 3. (R)-N-hydroxy-N-(3-butyn-2-yl)urea.

To a solution of (S)-O-p-toluenesulfonyl-3-butyn-2-ol (11.2 g, 50.0 mmol), prepared by addition of p-toluenesulfonyl chloride and triethylamine to (S)-3-butyn-2-ol, in methanol (100 mL), was added 55% aqueous hydroxylamine (30 mL, 0.50 mol) and the reaction mixture was stirred at ambient temperature for 40 hours. The reaction mixture was cooled to 10° C. and concentrated HCl (50 mL) was added dropwise. The reaction mixture was concentrated in vacuo and the residue was partitioned between H₂O (50 mL) and ethyl acetate (200 mL). The 2-phase mixture was cooled to 10° C. and taken to pH 8 with 50% aqueous NaOH solution (60 mL). After stirring for 15 min the layers were separated and the aqueous phase was extracted twice with 200 mL of ethyl acetate. The combined ethyl acetate extracts were cooled to 10° C. and a solution of KOCN (8.1 g, 0.10 mmol) in H₂O (30 mL) was added, followed by dropwise addition of 11 mL of concentrated HCl, and the reaction mixture was stirred for 30 min. The ethyl acetate layer was separated and the aqueous layer was extracted twice with ethyl acetate. The combined organic layers were dried over MgSO₄, filtered, and concentrated in vacuo to give 5.9 g (92% yield) of (R)-N-hydroxy-N-(3-butyn-2-yl)urea. mp 129° C. $[\alpha]_D^{24}$=+53.3° (c=0.58, CH₃OH). $^1$H NMR (DMSO-d₆, 300 MHz) δ1.25 (d, 3H, J=7 Hz), 3.05 (d, 1H, J=2.5 Hz), 4.85 (dq, 1H, J=2.5, 7 Hz), 6.50 (br s, 2H), 9.24 (s, 1H). $^{13}$CNMR (DMSO-d₆, 75 MHz) d 18.43, 45.14, 72.81, 83.87, 161.51. IR (KBr) 3455, 3330, 3290, 3215, 1658, 1637, 1585 cm⁻¹. MS (DCI/NH₃) m/e 146 (M+NH₄)⁺, 163 (M+NH₄.NH₃)⁺. Anal. Calc for C₅H₈N₂O₂: C, 46.87; H, 6.29; N, 21.86. Found: C, 46.78; H, 6.34; N, 21.72.

Step 4. (R)-N-{3-[5-(4-fluorophenylmethyl)thien-2-yl]-1-methyl-2-propynyl}-N-hydroxyurea.

To the (R)-N-hydroxy-N-(3-butyn-2-yl)urea prepared in step 3 above was added a solution of 2-iodo-5-(4-fluorophenylmethyl)thiophene (45 mmol), in isopropylacetate, followed by diisopropylamine (10 mL, 7.2 g, 71 mmol), bis(acetonitrile)palladium(II) chloride (65 mg, 0.25 mmol), copper(I)iodide (95 mg, 0.50 mmol), and triphenylphosphine (131 mg, 0.50 mmol), and the reaction mixture was stirred under nitrogen at ambient temperature for 2 hours. The reaction mixture was poured into 20% aqueous NH₄OH (200 mL) and stirred for 20 min. Heptane (300 mL) was added and the mixture was cooled in an ice-water bath and stirred for 15 min. The solid was filtered off, washed with H₂O, heptane, 25% CH₂Cl₂/heptane, and dried in vaucio to give 10.2 g (64% yield from (S)-O-p-toluenesulfonyl-3- butyn-2-ol) of (R)-N-{3-[5-(4-fluorophenylmethyl)thien-2-yl]-1-methyl-2-propynyl)-N-hydroxyurea (98% ee by chiral HPLC). m.p. 135°–136° C.(dec). $^1$H NMR (DMSO-d$_6$, 300 MHz) δ1.32 (d, J=6.0 Hz, 3H), 4.11 (s, 2H), 5.10 (q, J=6.0 Hz, 1H), 6.54 (s, 2H), 6.81 (d, J=3.0 Hz, 1H), 7.08 (d, J=3.0 Hz, 1H), 7.10–7.18 (m, 2H), 7.25–7.32 (m, 2H), 9.33 (s, 1H). MS (DCI/NH$_3$) m/e 319 (M+H)$^+$. [α]$_D^{23°}$=+47.8° (C=1 MeOH). Anal calcd for C$_{16}$H$_{15}$FN$_2$O$_2$S: C, 60.36; H, 4.75; N, 8.80. Found: C, 60.31; H, 4.79; N, 8.50.

EXAMPLE 13A

Alternative Method of Preparing (R)-N-{3-[5-(4-fluorophenylmethyl)thien-2-yl]-1-methyl-2-propynyl}-N-hydroxyurea.

Step 1. Preparation of 2-(4-fluorophenylmethyl)thiophene.

A mixture of 4-fluorobenzyl chloride (14.46 g, 0.1 mol) and NaI (18.0 g, 0.12 mol) in THF (50 ml) was heated to 65° C.~70° C. for 3 h (GC-MS showed that all the 4-fluorobenzyl chloride was converted to the 4-fluorobenzyl iodide). The mixture was cooled to room temperature and was used in the next step directly.

To a suspension of Mg (3 g, 0.123 mol) in THF (40 ml) was added a small amount of solid I$_2$ (20 mg). The mixture was heated to reflux under nitrogen. To the mixture was then added the 2-bromothiophene solution (5 ml) (19.6 g of 2-bromothiophene in 40 ml of THF). After the iodine color disappeared, to the suspension was added the rest of 2-bromothiophene solution dropwise keeping reflux. After the addition, the mixture was heated under reflux for 2 h., then was cooled to room temperature. To this mixture was added 4-fluorobenzyl iodide (or 4-fluorobenzyl bromide) followed by Li$_2$CuCl$_4$ (5 ml) solution keeping the temperature under 40° C. using a cool water bath. The mixture was stirred at room temperature for 2 h. To the mixture was added sat. NH$_4$Cl solution (100 ml), the mixture was stirred for 30 min., the organic layer was separated and washed with 10% sodium thiosulfate solution (50 ml), followed by distilled water (100 ml). The organic layer was then dried over MgSO$_4$ and concentrated to give 19 g of 2-(4-fluorobenzyl)thiophene as an oil. Purification was achieved by vacuum distillation (110° C., 5 mm Hg).

Step 2. Preparation of 5-((4-fluorophenyl)methyl)-2-iodothiophene

A mixture of 2-(4-fluorobenzyl)thiophene (8.4 g, 43.7 mmol), HIO$_3$ (1.86 g, 10.6 mmol), I$_2$ (4.86 g, 19.2 mmol), iso-propyl acetate (66 ml), acetic acid (7.7 ml) and conc. H$_2$SO$_4$ (0.79 ml) was heated at 35° C. overnight (GC-MS showed that all the starting material is converted to 5-(4-fluorobenzyl)-2-iodothiophene). To the reaction mixture was added brine solution (33 ml), the organic layer was separated and washed with sodium hydroxide/sodium thiosulfate solution (33 ml) (prepared from 2.3 g of NaOH, 3.3 g of Na$_2$S$_2$O$_3$ in 27 ml of H$_2$O), followed by 10% of NaHCO$_3$ solution (33 ml). The organic layer was filtered, the flitrate was used directly in the next step (assuming quantitative yield 13.9 g).

Step 3. Preparation of R-(+)-N-(3-butyn-2-yl)-N-hydroxyurea

A 1 L three-neck flask equipped with mechanical stirrer, reflux condensor and a dropping funnel was charged with S-butynol (35.0 g, 0.5 mol) in CH$_2$Cl$_2$ (500 mL). The mixture was cooled to 5° C. and triethylamine (65.5 g, 90 mL, 0.65 mol) was added. Methanesulfonyl chloride (78.5 g, 46 mL, 0.6 mol) was added dropwise keeping the temperature below 10° C. The reaction mixture was stirred at 5° C.–10° C. for 1.5 h and 0.5N HCl (300 mL) was cautiously added. The organic layer was separated and washed with saturated NaCl solution (2×150 mL). It was then dried (MgSO$_4$) and concentrated under vacuo to give 74.0 g (~100%) of the mesylate as a light yellow liquid. The mesylate was dissolved in methanol (500 mL) and 50% aqueous H$_2$NOH (300 mL, 5 mol) was added. The mixture was stirred at 23° C. for 16 hours and then concentrated under vacuo (below 40° C.) to 350 mL and pH of the mixture adjusted to pH 9 using 40% NaOH solution. The mixture was then extracted with ethyl acetate (5×300 mL). The combined ethyl acetate extract was cooled to 5° C. and a freshly prepared solution of KOCN (81.0 g, 1 mol) in water (150 mL) was added. Keeping the temperature below 10° C., conc. HCl (100 mL) was added dropwise. The mixture was stirred for 30 min, the organic layer was separated and the aqueous layer was extracted with (5×400 mL) ethyl acetate. The extracts were combined with the organic layer, dried (MgSO$_4$), concentrated under vacuo to ~150 mL, and heptane (600 mL) was added with vigorous stirring. The solid was filtered, washed with heptane and dried to give 55.0 g (86%) of R-(+)-N-(3-butyn-2-yl)-N-hydroxyurea as a light yellow solid.

Step 4. Preparation of R)-N-{3-[5-(4-fluorophenylmethyl)thien-2-yl]-1-methyl-2-propynyl}-N-hydroxyurea.

A 500 mL three-neck flask equipped with mechanical stirrer and nitrogen inlet was charged with 5-((fluorophen)methyl)-2-iodothiophene (31.8 g, 0.1 mol), N-((3-butyn-2-yl)-N-hydroxy)urea (12.8 g, 0.1 mol), (CH3CN)2PdCl2 (129 mg, 0.5 mmol), PPh3 (262 mg, 1.0 mmol), CuI (190 mg, 1.0 mmol) and isopropyl acetate (200 mL). To this mixture, di-isopropylamine (11.1 g, 15.4 mL, 0.11 mol) was added and it was stirred at 23° C. for 2.5 h. A solution of ammonium hydroxide (20%, 150 mL) was added and the mixture was stirred for 30 min. Heptane (400 mL) was added and the mixture was stirred for 15 min. The solid product was filtered, washed with water (2×100 mL), heptane (2×100 mL) and dried to give A-85761 (28.2 g, 88.7%) as a light yellow solid. The crude product was recrystallized from EtOAc/heptane

EXAMPLE 14

Preparation of N-{3-[5-(4-fluorophenylcarbonyl)thien-2-yl]-1-methyl-2-propynyl}-N-hydroxyurea.

Step 1. N-methoxy-N-methyl-4-fluorobenzamide.

To a 0° C. solution of 4-fluorobenzoyl chloride (11.9 g, 75.0 mmol) in CH$_2$Cl$_2$ (150 mL) was added N,O-dimethylhydroxylamine hydrochloride (8.00 g, 82.0 mmol) and a solution of pyridine (13.0 g, 164 mmol) in CH$_2$Cl$_2$ (25 mL). The cold bath was removed and the reaction mixture was stirred for 2 hours at ambient temperature and then was washed with 0.5N aqueous HCl (3×100 mL), saturated aqueous NaHCO$_3$, and brine. The organic phase was dried over MgSO$_4$, filtered, and concentrated in vacuo to give N-methoxy-N-methyl-4-fluorobenzamide (13.3 g, 97%) as an oil.

Step 2. 2-bromo-5-(4-fluorophenylcarbonyl)thiophene.

A solution of 2,5-dibromothiophene (19.23 g, 75.5 mmol) in anhydrous THF (400 mL) was treated at −78° C. under nitrogen with a 2.5M solution of n-butyllithium in hexane (30.0 mL, 75.5 mmol). The resulting solution was stirred for 45 minutes at −78° C. and then transferred by cannula into a cold (−78° C.) solution of N-methoxy-N-methyl-4-fluorobenzamide (12.57 g, 68.6 mmol), prepared as in step 1, in anhydrous THF (300 mL) with siring. After 30 minutes at −78° C., the reaction was quenched by the addition of a saturated solution of NH$_4$Cl (15 mL) and poured into ethanol (350 mL) containing 10% HCl (140 mL). The mixture was partitioned between brine and 1:1 ether and dichloromethane. The organic layer was dried over $Na_2SO_4$ and concentrated in vacuo. The residue was crystallized from pentane to give 16.8 g (86%) of 2-bromo-5-(4-fluorophenylcarbonyl)thiophene.

Step 3. N-{3-[5-(4-fluorophenylcarbonyl)thien-2-yl]-1-methyl-2-propynyl}-N-hydroxyurea The desired compound was prepared according to the method of Example 1, steps 3–5, except substituting 2-bromo-5-(4-fluorophenylcarbonyl)thiophene, prepared as in step 2, for 2-bromo-5-(4-fluorophenylmethyl)furan. m.p. 136.5°–138° C.(dec). $^1$H NMR (DMSO-$d_6$, 300 MHz) δ1.38 (d, J=6.0 Hz, 3H), 5.21 (q, J=6.0 Hz, 1H), 6.62 (s, 2H), 7.36–7.45 (m, 3H), 7.65 (d, J=3.0 Hz, 1H), 7.90–7.79 (m, 2H), 9.46 (s, 1H). MS (DCI/$NH_3$) m/e 333 (M+H)$^+$. Anal calcd for $C_{16}H_{13}FN_2O_3S$: C, 57.82; H, 3.94; N, 8.43. Found: C, 57.85; H, 3.84; N, 8.43.

EXAMPLE 15

Preparation of (R)-N-(3-(5-(4-fluorophenylcarbonyl)thien-2-yl)-1-methyl-2-propynyl)-N-hydroxyurea.

The desired compound was prepared according to the method of Example 13, except substituting 2-bromo-5-(4-fluorophenylcarbonyl)thiophene, prepared as in Example 14, step 2, for 2-iodo-5-(4-fluorophenylmethyl)thiophene. mp 146°–147° C. $^1$H NMR (DMSO-$d_6$) δ1.39 (d, J=7 Hz, 3H), 5.21 (q, J=7 Hz, 1H), 6.59 (bs, 2H), 7.38 (d, J=4 Hz, 1H), 7.41 (m, 2H), 7.65 (d, J=4 Hz, 1H), 7.93 (m, 2H), 9.43 (s, 1H). MS (DCI/$NH_3$) m/e 350(M+$NH_4$)$^+$, 333 (M+1)$^+$, 272. Anal calcd for $C_{16}H_{13}FN_2O_3S$: C, 57.82 H, 3.94; N, 8.43. Found: C, 57.37; H, 3.84; N, 8.35.

EXAMPLE 16

Preparation of (R)-N-{3-[5-(3-chloropyrid-3-ylmethyl)thien-2-yl]-1-methyl-2-propynyl}-N-hydroxyurea The title compound is prepared using the procedures described in Example 13, except substituting 2-(3-chloropyrid-3-ylmethyl)thiophene for 2-(4-fluorophenylmethyl)thiophene.

EXAMPLE 17

Preparation of (R)-N-{3-[5-(3-chloropyrid-3-ylmethyl)fur-2-yl]-1-methyl-2-propynyl}-N-hydroxyurea.

The title compound is prepared using the procedures described in Example 13, except substituting 2-(3-chloropyrid-3-ylmethyl)furan for 2-(4-fluorophenylmethyl)thiophene.

EXAMPLE 18

Preparation of (R)-N-{3-[5-(3-chloropyrid-3-ylmethyl)phenyl]-1-methyl-2-propynyl}-N-hydroxyurea.

The title compound is prepared using the procedures described in Example 13, except substituting (3-chloropyrid-3-ylmethyl)benzene for 2-(4-fluorophenylmethyl)thiophene.

EXAMPLE 19

Preparation of (R)-N-{3-[5-(4-chlorophenylmethyl)thien-2-yl]-1-methyl-2-propynyl}-N-hydroxyurea.

Step 1. 4-chlorobenzyl bromide.

To a suspension of 4-chlorobenzyl alcohol (14.26 g, 100 mmol) in $CH_2Cl_2$ (40 mL) at ambient temperature was added added dropwise a solution of $PBr_3$ in $CH_2Cl_2$(1.0M, 32 mL, 32 mmol). The reaction mixture was stirred for 72 hours at ambient temperature and then was poured slowly onto ice. The layers were separated and the organic phase was dried over $MgSO_4$, filtered, and concentrated in vacuo to give 4-chlorobenzyl bromide (19.76 g) as a colorless solid.

Step 2. 2-(4-chlorophenylmethyl)thiophene.

The desired compound was prepared according to the method of Example 12, step 1, except substituting 4-chlorobenzyl bromide, prepared as in step 1, for 4-fluorobenzyl bromide, and using THF instead of the ether/THF mixture.

Step 3. 2-iodo-5-(4-chlorophenylmethyl)thiophene.

The desired compound was prepared according to the method of Example 12, step 2, except substituting N-iodosuccinimide for N-bromosuccinimide and substituting 2-(4-chlorophenylmethyl)thiophene, prepared as in step 2 for 2-(4-fluorophenylmethyl)thiophene.

Step 4. (R)-N-{3-[5-(4-chlorophenylmethyl)thien-2-yl]-1-methyl-2-propynyl}-N-hydroxyurea.

The title compound was prepared using the procedures described in Example 13, step 4, except substituting 2-iodo-5-(4-chlorophenylmethyl)thiophene, prepared as in step 3, for 2-iodo-5-(4-fluorophenylmethyl)thiophene. mp 132°–134° C. $^1$H NMR (DMSO-$d_6$) δ1.33 (d, J=7 Hz, 3H), 4.12 (s, 2H), 5.11 (q, J=7 Hz, 1H), 6.50 (bs, 2H), 6.82 (d, J=4 Hz, 1H), 7.08 (d, J=4 Hz, 1H), 7.28 (m, 2H), 7.37 (m, 2H), 9.30 (s, 1H). MS (DCI/$NH_3$) m/e 352 (M+$NH_4$)$^+$, 335 (M+H)$^+$, 259. Anal calcd for $C_{16}H_{15}N_2O_2S$: C, 57.40; H, 4.52; N, 8.37. Found: C, 57.46; H, 4.26; N, 8.40.

EXAMPLE 20

Preparation of (R)-N-{3-[5-(4-fluorophenylmethyl)thiazo-2-yl]-1-methyl-2-propynyl}-N-hydroxyurea.

The title compound is prepared using the procedures described in Example 13, except substituting 5-(4-fluorophenylmethyl)thiazole for 2-(4-fluorophenylmethyl)thiophene.

EXAMPLE 21

Preparation of (R)-N-(3-(5-(3-pyridylmethyl)thien-2-yl)-1-methyl-2-propynyl)-N-hydroxyurea.

Step 1. 2-(3-pyridylhydroxymethyl)thiophene.

To a solution of 3-pyridinecarboxaldehyde (5.0 mL, 53 mmol) in THF at −78° C. was added 2-thienyllithium (1.0M in THF. 64 mL, 64 mmol) and the reaction mixture was stirred for 2 hours at −78° C. The reaction mixture was quenched with saturated aqueous $NH_4Cl$ and extracted with ether. The organic phase was dried over $MgSO_4$, filtered, and concentrated in vacuo. Chromatography on silica gel (5%, then 10% methanol/$CHCl_3$) gave 2-(3-pyridylhydroxymethyl)thiophene (6.30 g, 62% yield).

Step 2. 2-(3-pyridylmethyl)thiophene.

To a solution of 2-(3-pyridylhydroxymethyl)thiophene (8.82 g, 46.2 mmol), prepared as in step 1, in acetic acid (50 mL) was added tin(II)chloride dihydrate (22.9 g, 101 mmol) and HCl gas was bubbled through the reaction mixture for about 10 min. The reaction mixture was stirred for 1.5 hours at ambient temperature, and the liquid was decanted, concentrated in vacuo to a volume of about 10 mL, and poured into $H_2O$. The aqueous solution was made basic by the slow addition of saturated aqueous $NaHCO_3$ and extracted with ethyl acetate/ether. The organic phase was dried over $MgSO_4$, filtered, and concentrated in vacuo. Chromatography on silica gel (5% methanol/$CHCl_3$) gave 2-(3-pyridylmethyl)thiophene (2.63 g).

Step 3. (R)-N-(3-(5-(3-pyridylmethyl)thien-2-yl)-1-methyl-2-propynyl)-N-hydroxyurea.

The desired compound was prepared according to the method of Example 19, steps 3 and 4, except substituting 2-(3-pyridylmethyl)thiophene for 2-(4-chlorophenylmethyl)thiophene. mp 108°–110° C. $^1$H NMR (DMSO-d$_6$) δ1.32 (d, J=7 Hz, 3H), 4.17 (s, 2H), 5.10 (q, J=7 Hz, 1H), 6.54 (s, 2H), 6.83 (d, J=4.0 Hz, 1H), 7.08 (d, J=4 Hz, 1H), 7.34 (m, 1H), 7.67 (m, 1H), 8.44 (m, 1H), 8.52 (m, 1H), 9.32 (s, 1H). MS (DCI/NH$_3$) m/e 319 (M+NH$_4$)$^+$, 302 (M+H)$^+$, 259. Anal calcd for C$_{15}$H$_{15}$N$_3$O$_2$S: C, 59.78; H, 5.02; N, 13.94. Found: C, 59.81; H, 4.86; N, 13.81.

EXAMPLE 22

Preparation of (R)-N-(3-(5-(4-fluorophenylmethyl)-4-methylthien-2-yl)-1-methyl-2-propynyl)-N-hydroxyurea.
Step 1. 2-(4-fluorophenylmethyl)-3-methylthiophene.

The desired compound was prepared according to the method of Example 12, step 1, except substituting 2-bromo-3-methylthiophene for thiophene, and using THF instead of the ether/THF mixture.
Step 2. (R)-N-(3-(5-(4-fluorophenylmethyl)-4-methylthien-2-yl)-1-methyl-2-propynyl)-N-hydroxyurea.

The desired compound was prepared according to the method of Example 19 steps 3 and 4, except substituting 2-(4-fluorophenylmethyl)-3-methylthiophene, prepared as in step 1, for 2-(4-chlorophenylmethyl)thiophene. mp 136°–137° C. (dec.). $^1$H NMR (DMSO-d$_6$) δ1.31 (d, J=7 Hz, 3H), 2.09 (s, 3H), 4.03 (s, 2H), 5.09 (q, J=7 Hz, 1H), 6.53 (bs, 2H), 6.98 (s, 1H), 7.12 (m, 2H), 7.24 (m, 2H), 9.31 (s, 1H). MS (DCI/NH$_3$) m/e 333 (M+H)$^+$, 257.

EXAMPLE 23

Preparation of (R)-N-{3-(5-(thien-2-ylmethyl)thien-2-yl)-1-methyl-2-propynyl)-N-hydroxyurea.

The desired compound was prepared according to the method of Example 19, steps 3 and 4, except substituting 2-(thien-2-ylmethyl)thiophene for 2-(4-chlorophenylmethyl)thiophene. mp 127°–128° C. (dec.). $^1$H NMR (DMSO-d$_6$) δ1.33 (d, J=7 Hz, 3H), 4.35 (s, 2H), 5.11 (q, J=7 Hz, 1H), 6.54 (bs, 2H), 6.86 (d, J=4 Hz, 1H), 6.96 (m, 2H), 7.08 (d, J=4 Hz, IH), 7.38 (dd, J=4 Hz, 2 Hz, 1H)), 9.34 (s, 1H). MS (DCI/NH$_3$) m/e 324 (M+NH$_4$)$^+$, 307 (M+H)$^+$, 231.

EXAMPLE 24

Preparation of (R)-N-(3-(5-(4-pyridylmethyl)thien-2-yl)-1-methyl-2-propynyl)-N-hydroxyurea.
Step 1. 2-iodo-5-(4-pyridylhydroxymethyl)thiophene.

To a solution of LDA (11 mmol) in THF at −78° C. was added 2-iodothiophene (2.1 g, 10 mmol). After stirring for 0.5 hours at −78° C., a solution of 4-pyridinecarboxaldehyde (1.07 g, 10 mmol) in THF (10 mL) was added dropwise and the reaction mixture was warmed slowly to ambient temperature and stirred for a further 16 hours. The reaction was quenched with saturated aqueous NH$_4$Cl, diluted with H$_2$O, and extracted twice with ethyl acetate. The combined organic layers were dried over MgSO$_4$, filtered, and concentrated in vacuo. Chromatography on silica gel (80% ethyl acetate/hexanes) provided 2-iodo-5-(4-pyridiylhydroxymethyl)thiophene (1.39 g, 40% yield) as a tan solid.
Step 2. 2-iodo-5-(4-pyridylmethyl)thiophene.

A suspension of 2-iodo-5-(4-pyridiylhydroxymethyl)thiophene (0.65 g, 2.05 mmol) and tin(II) chloride dihydrate (1.01 g, 4.51 mmol) in acetic acid (5 mL) was treated with HCl gas for 10 min and stirred for 2 hours at ambient temperature. The reaction mixture was poured into H$_2$O, neutralized with 10% aqueous NaOH, and extracted twice with ethyl acetate. The combined organic layers were washed with H$_2$O, dried over MgSO$_4$, filtered, and concentrated in vacuo. Chromatography on silica gel provided 2-iodo-5-(4-pyridylmethyl)thiophene (0.22 g, 36% yield) as a white solid.
Step 3. (R)-N-(3-(5-(4-pyridylmethyl)thien-2-yl)-1-methyl-2-propynyl)-N-hydroxyurea.

The desired compound was prepared according to the method of Example 13, step 4, except substituting 2-iodo-5-(4-pyridylmethyl)thiophene, prepared as in step 2, for 2-iodo-5-(4-fluorophenylmethyl)thiophene. mp 154°–156° C. $^1$H NMR (DMSO-d$_6$) δ1.32 (d, J=7 Hz, 3H), 4.17 (s, 2H), 5.11 (q, J=7 Hz, 1H), 6.54 (bs, 2H), 6.87 (d, J=4 Hz, 1H), 7.10 (d, J=4 Hz, 1H), 7.25 (m, 2H), 8.49 (m, 2H), 9.32 (s, 1H). MS (DCI/NH$_3$) m/e 302 (M+H)$^+$, 259, 243. Anal calcd for C$_{15}$H$_{15}$N$_3$O$_2$S: C, 59.78; H, 5.02; N, 13.94. Found: C, 59.40; H, 4.97; N, 13.73.

EXAMPLE 25

Preparation of (R)-N-(3-(5-(2-naphthylmethyl)thien-2-yl)-1-methyl-2-propynyl)-N-hydroxyurea.
Step 1. 2-iodo-5-(2-naphthylmethyl)thiophene.

The desired compound was prepared according to the method of Example 24, step 1, except substituting 2-(bromomethyl)naphthylene for 4-pyridinecarboxaldehyde.
Step 2. (R)-N-(3-(5-(2-naphthylmethyl)thien-2-yl)-1-methyl-2-propynyl)-N-hydroxyurea.

The desired compound was prepared according to the method of Example 13, step 4, except substituting 2-iodo-5-(2-naphthylmethyl)thiophene, prepared as in step 1, for 2-iodo-5-(4-fluorophenylmethyl)thiophene. mp 134.5°–135° C. $^1$H NMR (DMSO-d$_6$) δ1.31 (d, J=7.5 Hz, 3H), 4.30 (s, 2H), 5.11 (q, J=7.5 Hz, 1H), 6.53 (s, 2H), 6.88 (d, J=4 Hz, 1H), 7.09 (d, J=4 Hz, 1H), 7.41 (m, 1H), 7.49 (m, 2H), 7.77 (s, 1H), 7.87 (m, 3H), 9.31 (s, 1H). MS (DCI/NH$_3$) m/e 368 (M+NH$_4$)$^+$, 351 (M+H)$^+$. Anal calcd for C$_{20}$H$_{18}$N$_2$O$_2$S: C, 68.54; H, 5.18; N, 7.99. Found: C, 68.44; H, 4.99; N, 7.92.

EXAMPLE 26

Preparation of (R)-N-(3-(5-(4-fluorophenylhydroxymethyl)thien-2-yl)-1-methyl-2-propynyl)-N-hydroxyurea.

The desired compound was prepared according to the method of Example 25, except substituting 4-fluorobenzaldehyde for 2-(bromomethyl)naphthylene. $^1$H NMR (DMSO-d$_6$) δ1.33 (d, J=7 Hz, 3H), 5.11 (q, J=7 Hz, 1H), 6.41 (d, J=5 Hz, 1H), 6.55 (s, 2H), 6.76 (d, J=5 Hz, 1H), 7.05 (d, J=4 Hz, 1H), 7.05 (d, J=4 Hz, 1H), 7.17 (m, 2H), 7.43 (m, 2H), 9.32 (s, 1H). MS (DCI/NH$_3$) m/e 352 (M+NH$_4$)$^+$, 335 (M+H)$^+$, 274, 259. Anal calcd for C$_{16}$H$_{15}$N$_2$O$_3$S: C, 57.47 H, 4.52; N, 8.38. Found: C, 56.94; H, 4.48; N, 8.29.

EXAMPLE 27

Preparation of (R)-N-(3-(5-(2-quinolylmethyl)thien-2-yl)-1-methyl-2-propynyl)-N-hydroxyurea.

The desired compound was prepared according to the method of Example 24, except substituting 2-quinolinecarboxaldehyde for 4-pyridinecarboxaldehyde. $^1$H NMR (DMSO-d$_6$) δ1.33 (d, J=7.5 Hz, 3H), 4.87 (s, 2H), 5.10 (q, J=7.5 Hz, 1H), 6.54 (bs, 2H), 6.94 (d, J=4 Hz, 1H), 7.09 (d, J=4 Hz, 1H), 7.49 (d, J=9 Hz, 1H), 7.58 (m, 4H), 7.76 (m, 1H), 7.97 (m, 1H), 8.33 (d, J=9 Hz, 1H), 9.32 (s, 1H). MS (DCI/NH$_3$) m/e 352 (M+H)$^+$, 293. Anal calcd for $C_{19}H_{17}N_3O_2S$: C, 64.94; H, 4.88; N, 11.96. Found: C, 64.58; H, 4.89; N, 11.62.

EXAMPLE 28

Preparation of N-(3-(5-(4-fluorophenylmethyl)thien-2-yl)-2-propynyl)-N-hydroxyurea.
Step 1. N-hydroxy-N-(2-propynyl)urea.

The desired compound was prepared according to the method of Example 4, steps 1 and 2, except substituting propargyl alcohol for 3-butyn-2-ol.
Step 2. N-(3-(5-(4-fluorophenylmethyl)thien-2-yl)-2-propynyl)-N-hydroxyurea.

The desired compound was prepared according to the method of Example 13, step 4, except substituting N-hydroxy-N-(2-propynyl)urea, prepared as in step 1, for (R)-N-hydroxy-N-(3-butyn-2-yl)urea. mp 145°–146° C. (dec.). $^1$H NMR (DMSO-$d_6$) δ4.12 (s, 2H), 4.31 (s, 2H), 6.53 (s, 2H), 6.82 (d, J=4 Hz, 1H), 7.11 (d, J=4 Hz, 1H), 7.14 (m, 2H), 7.29 (m, 2H), 9.58 (s, 1H). MS (DCI/NH$_3$) m/e 322 (M+NH$_4$)$^+$, 305 (M+H)$^+$, 244.

EXAMPLE 29

Preparation of (R)-N-(3-(5-(4-fluorophenylmethyl)-3-chlorothien-2-yl)-1-methyl-2-propynyl)-N-hydroxyurea.
Step 1. 2-iodo-3-chlorothiophene.

The desired compound was prepared according to the method of Example 19, step 3, except substituting 3-chlorothiophene for 2-(4-chlorophenylmethyl)thiophene.
Step 2. 2-iodo-3-chloro-5-(4-fluorophenylmethyl)thiophene.

The desired compound was prepared according to the method of Example 24, step 1, except substituting 2-iodo-3-chlorothiophene, prepared as in step 1, for 2-iodothiophene, and substituting 4-fluorobenzyl bromide for 4-pyridinecarboxaldehyde
Step 3. (R)-N-(3-(5-(4-fluorophenylmethyl)-3-chlorothien-2-yl)-1-methyl-2-propynyl)-N-hydroxyurea.

The desired compound was prepared according to the method of Example 13, step 4, except substituting 2-iodo-3-chloro-5-(4-fluorophenylmethyl)thiophene, prepared as in step 2, for 2-iodo-5-(4-fluorophenylmethyl)thiophene. mp 131°–132° C. $^1$H NMR (DMSO-$d_6$) δ1.33 (d, J=7 Hz, 3H), 4.10 (s, 2H), 5.12 (q, J=7 Hz, 1H), 6.57 (bs, 2H), 7.10–7.34 (m, 5H), 9.36 (s, 1H). MS (DCI/NH$_3$) m/e 353 (M+H)$^+$, 292, 277. Anal calcd for $C_{16}H_{14}ClFN_2O_2S$: C, 54.47; H, 4.00 N, 7.94. Found: C, 54.42: H, 3.80; N, 7.83.

EXAMPLE 30

Preparation of (R)-N-(3-(5-(4-fluorophenoxymethyl)thien-2-yl)-1-methyl-2-propynyl)-N-hydroxyurea.
Step 1. 2-thienylmethyl methanesulfonate.

To a 0° C. mixture of 2-thiophenemethanol (2.80 g, 24.5 mmol) and triethylamine (5.10 mL, 36.8 mmol) in $CH_2Cl_2$ (25 mL) was added methanesulfonyl chloride (2.09 mL, 27.0 mmol) and the reaction mixture was stirred for 2 hours. The reaction mixture was poured into $H_2O$ and the layers were separated. The organic phase was washed with cold 1N HCl (3×), saturated aqueous NaHCO$_3$, and brine, dried over MgSO$_4$, filtered. and concentrated in vacuo. 2-thienylmethyl methanesulfonate (1.78 g, 38%) was obtained by chromatography on silica gel (20% ethyl acetate/hexane).
Step 2. 2-(4-fluorophenoxymethyl)thiophene.

The desired compound (1.86 g) was prepared by addition of NaH (80% dispersion in mineral oil, 306 mg, 10.2 mmol) to a solution in DMSO of 2-thienylmethyl methanesulfonate (1.78 g, 9.27 mmol), prepared in step 1, followed by addition of 4-fluorophenol (1.04 g, 9.27 mmol).
Step 3. (R)-N-(3-(5-(4-fluorophenoxymethyl)thien-2-yl)-1-methyl-2-propynyl)-N-hydroxyurea.

The desired compound was prepared according to the method of Example 19, steps 3 and 4, except substituting 2-(4-fluorophenoxymethyl)thiophene, prepared as in step 2, for 2-(4-chlorophenylmethyl)thiophene. $^1$H NMR (DMSO-$d_6$) δ1.35 (d, J=7.5 Hz, 3H), 5.13 (q, J=7.5 Hz, 1H), 5.25 (s, 2H), 6.57 (bs, 2H), 7.02 (m, 2H), 7.12 (m, 4H), 9.35 (s, 1H). MS (DCI/NH$_3$) m/e 352 (M+NH$_4$)$^+$, 335 (M+H)$^+$. Anal calcd for $C_{16}H_{15}FN_2O_3S$: C, 57.47; H, 4.52; N, 8.38. Found: C, 57.30; H, 4.57; N, 8.55.

EXAMPLE 31

Preparation of (R)-N-(3-(5-(4-fluorophenylethyl)thien-2-yl)-1-methyl-2-propynyl)-N-hydroxyurea.

The desired compound was prepared according to the method of Example 19. except substituting 4-fluorophenethyl alcohol for 4-chlorobenzyl alcohol. mp 126°–128° C. $^1$H NMR (DMSO-$d_6$) δ1.33(d, J=7 Hz, 3H), 2.90 (m, 2H), 3.07 (m, 2H), 5.12 (q, J=7 Hz, 1H), 6.54 (s, 2H), 6.73 (d, J=4 Hz, 1H), 7.03 (d, J=4 Hz, 1H), 7.09 (m, 2H), 7.24 (m, 2H), 9.34 (s, 1H). MS (DCI/NH$_3$) m/e 350 (M+NH$_4$)$^+$, 332 (M+H)$^+$, 257. Anal calcd for $C_{17}H_{17}FN_2O_3S$: C, 61.43; H, 5.16; N, 8.43. Found: C, 61.36; H, 5.10; N, 8.42.

EXAMPLE 32

Preparation of (R)-N-(3-(5-(2-pyridylhydroxymethyl)thien-2-yl)-1-methyl-2-propynyl)-N-hydroxyurea.

The desired compound was prepared according to the method of Example 26, except substituting 2-pyridinecarboxaldehyde for 4-fluorobenzaldehyde. $^1$H NMR (DMSO-$d_6$) δ1.37 (d, J=7 Hz, 3H), 5.15 (q, J=7 Hz, 1H), 5.92 (d, J=5 Hz, 1H), 6.58 (m, 3H), 6.87 (dd, J=4 Hz, 1H), 7.08 (d, J=4 Hz, 1H), 7.32 (m, 1H), 7.59 (d, J=8 Hz, 1H), 7.85 (m, 1H), 8.53 (m, 1H), 9.37(s, 1H). MS (DCI/NH$_3$) m/e 318 (M+H)$^+$, 275. Anal calcd for $C_{15}H_{15}N_3O_3S$: C, 56.77; H, 4.76; N, 13.24. Found: C, 56.40; H, 4.69; N, 12.78.

EXAMPLE 33

Preparation of (R)-N-(3-(5-(4-fluorophenylmethoxymethyl)thien-2-yl)-1-methyl-2-propynyl)-N-hydroxyurea.
Step 1. 2-(4-fluorophenylmethoxymethyl)thiophene.

To a solution in DMSO (30 mL) of 4-fluorobenzyl bromide (3.27 mL, 26.3 mmol), 2-thiophenemethanol (3.00 mL, 31.7 mmol), and benzyltrimethylammonium chloride (244 mg, 1.31 mmol) was added NaOH (6.31 g, 159 mmol) and the reaction mixture was stirred for 17 hours at ambient temperature. The reaction mixture was poured into brine and extracted with ether. The organic phase was washed with 1N aqueous $H_3PO_4$ (3×), $H_2O$ (3×), saturated aqueous NaHCO$_3$ (2×), and brine, dried over MgSO$_4$, filtered, and concentrated in vacuo. Chromatography on silica gel (20% ethyl acetate/hexane) gave 2-(4-fluorophenylmethoxymethyl)thiophene (5.03 g, 86%).
Step 2. (R)-N-(3-(5-(4-fluorophenylmethoxymethyl)thien-2-yl)-1-methyl-2-propynyl)-N-hydroxyurea.

The desired compound was prepared according to the method of Example 19, steps 3 and 4, except substituting 2-(4-fluorophenylmethoxymethyl)thiophene, prepared as in step 1, for 2-(4-chlorophenylmethyl)thiophene. mp 90°–91° C. $^1$H NMR (DMSO-$d_6$) δ1.35 (d, J=7 Hz, 3H), 4.50 (s, 2H), 4.67 (s, 2H), 5.14 (q, J=7 Hz, 1H), 6.56 (s, 2H), 6.98 (d, J=4 Hz, 1H), 7.13 (d, J=4 Hz, 1H), 7.18 (m, 2H), 7.38 (m, 2H), 9.36 (s, 1H). MS (DCI/NH$_3$) m/e 366 (M+NH$_4$)$^+$, 349 (M+H)$^+$. Anal calcd for C$_{17}$H$_{17}$FN$_2$O$_3$S: C, 58.60; H, 4.92; N, 8.04. Found: C, 58.17; H, 4.89; N, 8.11.

EXAMPLE 34

Preparation of (R)-N-(3-(5-(2-pyridylmethyl)thien-2-yl)-1-methyl-2-propynyl)-N-hydroxyurea.
Step 1. 2-(2-pyridylmethyl)thiophene.

The desired compound was prepared according to the method of Example 24, steps 1 and 2, except substituting 2-pyridinecarboxaldehyde for 4-pyridinecarboxaldehyde.
Step 2. (R)-N-(3-(5-(2-pyridylmethyl)thien-2-yl)-1-methyl-2-propynyl)-N-hydroxyurea.

The desired compound was prepared according to the method of Example 19, steps 3 and 4, except substituting 2-(2-pyridylmethyl)thiophene, prepared as in step 1, for 2-(4-chlorophenylmethyl)thiophene. mp 62°–65° C. $^1$H NMR (DMSO-d$_6$) δ1.33 (d, J=7 Hz, 3H), 4.25 (s, 2H), 5.11 (q, J=7.5 Hz, 1H), 6.53 (bs, 2H), 6.85 (d, J=4 Hz, 1H), 7.06 (d, J=4 Hz, 1H), 7.25 (m, 1H), 7.32 (m, 1H), 7.73 (m, 1H), 8.51 (m, 1H), 9.32 (s, 1H). MS (DCI/NH$_3$) m/e 319 (M+NH$_4$)$^+$, 302 (M+H)$^+$, 241. Anal calcd for C$_{15}$H$_{15}$N$_3$O$_2$S: C, 59.78; H, 5.02; N, 13.94. Found: C, 59.64; H, 4.95; N, 13.13.

EXAMPLE 35

Preparation of (R)-N-(3-(3-(4-fluorophenylmethyl)thien-2-yl)-1-methyl-2-propynyl)-N-hydroxyurea.
Step 1. 3-(4-fluorophenylmethyl)thiophene.

The desired compound was prepared according to the method of Example 13, step 1, except substituting 3-bromothiophene for 2-bromothiophene.
Step 2. (R)-N-(3-(3-(4-fluorophenylmethyl)thien-2-yl)-1-methyl-2-propynyl)-N-hydroxyurea.

The desired compound was prepared according to the method of Example 19, steps 3 and 4, except substituting 3-(4-fluorophenylmethyl)thiophene, prepared as in step 1, for 2-(4-chlorophenylmethyl)thiophene. mp 99°–100° C. $^1$H NMR (DMSO-d$_6$) δ1.38 (d, J=7.5 Hz, 3H), 3.92 (s, 2H), 5.18 (q, J=7.5 Hz, 1H), 6.61 (s, 2H), 6.97 (d, J=4.5 Hz, 1H), 7.10 (m, 2H), 7.33 (m, 2H), 7.43 (d, J=4.5 Hz, 1H), 9.38 (s, 1H). MS (DCI/NH$_3$) m/e 336 (M+NH$_4$)$^+$, 319 (M+H)$^+$. Anal calcd for C$_{16}$H$_{15}$FN$_2$O$_2$S: C, 60.36; H, 4.75: N, 8.80. Found: C, 60.23; H, 4.64; N, 8.63.

EXAMPLE 36

Preparation of (R)-N-(3-(4-(4-fluorophenylmethyl)thien-2-yl)-1-methyl-2-propynyl)-N-hydroxyurea.
Step 1. 2-iodo-4-(4-fluorophenylmethyl)thiophene.

To a solution of LDA (3.67 mmol) in THF at −78° C. was added a solution of 3-(4-fluorophenylmethyl)thiophene (640 mg, 3.33 mmol), prepared as in Example 35, step 1, and the reaction mixture was stirred for 25 min. A solution of I$_2$ (1.01 g, 4.00 mmol) in THF was added and the cold bath was removed. The reaction mixture was warmed to ambient temperature, quenched with saturated aqueous NH$_4$Cl, and extracted with ether. The organic phase was washed with 1N aqueous H$_3$PO$_4$, saturated aqueous NaHCO$_3$, saturated aqueous Na$_2$S$_2$O$_3$, and brine, dried over MgSO$_4$, filtered, and concentrated in vacuo to give 928 mg of 2-iodo-4-(4-fluorophenylmethyl)thiophene which was used without further purification.

Step 2. (R)-N-(3-(4-(4-fluorophenylmethyl)thien-2-yl)-1-methyl-2-propynyl)-N-hydroxyurea.

The desired compound was prepared according to the method of Example 13, step 4, except substituting 2-iodo-4-(4-fluorophenylmethyl)thiophene, prepared as in step 1, for 2-iodo-5-(4-fluorophenylmethyl)thiophene. mp 105°–108° C. $^1$H NMR (DMSO-d$_6$) δ1.32 (d, J=7.5 Hz, 3H), 3.87 (s, 2H), 5.11 (q, J=7.5 Hz, 1H), 6.54 (s, 2H), 7.11 (m, 3H), 7.24 (m, 3H), 9.34 (s, 1H). MS (DCI/NH$_3$) m/e 336 (M+NH$_4$)$^+$, 319 (M+H)$^+$. Anal calcd for C$_{16}$H$_{15}$FN$_2$O$_2$S: C, 60.36; H, 4.75; N, 8.80. Found: C, 60.09; H, 4.43; N, 8.72.

EXAMPLE 37

Preparation of (R)-N-(3-(5-(pyrrolodin-2-one-1-methyl)thien-2-yl)-1-methyl-2-propynyl)-N-hydroxyurea.
Step 1. 2-(pyrrolodin-2-one-1-ylmethyl)thiophene.

A mixture of ethyl 4-bromobutyrate (5.85 g, 30.0 mmol), 2-thiophenemethylamine (13.6 g, 120 mmol), and N,N-diisopropylethylamine (3.88 g, 30.0 mmol) in benzene (100 mL) was stirred under N$_2$ at reflux for 2 hours. The reaction mixture was cooled to ambient temperature and filtered. The residue was concentrated in vacuo, dissolved in ether, and washed twice with 2N aqueous HCl, and once with brine, then dried over MgSO$_4$, filtered, and concentrated in vacuo to give 2-(pyrrolodin-2-one-1-ylmethyl)thiophene (2.59 g) as an oil.
Step 2. (R)-N-(3-(5-(pyrrolodin-2-one-1-methyl)thien-2-yl)-1-methyl-2-propynyl)-N-hydroxyurea.

The desired compound was prepared according to the method of Example 19, steps 3 and 4, except substituting 2-(pyrrolodin-2-one-1-ylmethyl)thiophene, prepared as in step 1, for 2-(4-chlorophenylmethyl)thiophene. mp 156°–158° C. $^1$H NMR (DMSO-d$_6$) δ1.34 (d, J=7 Hz, 3H), 1.91 (m, 2H), 2.25 (d, J=8 Hz, 2H), 3.27 (d, J=8 Hz, 2H), 4.50 (s, 2H), 5.12 (q, J=7 Hz, 1H), 6.55 (s, 2H), 6.92 (d, J=4 Hz, 1H), 6.99 (d, J=4 Hz, 1H), 9.35 (s, 1H). MS (DCI/NH$_3$) m/e 308 (M+H)$^+$. Anal calcd for C$_{14}$H$_{17}$N$_3$O$_3$S: C, 54.71; H, 5.57; N, 13.67. Found: C, 54.08; H, 5.54; N, 13.48.

EXAMPLE 38

Preparation of (R)-N-(3-(3,4-bis-(4-fluorophenylmethyl)thien-2-yl)-1-methyl-2-propynyl)-N-hydroxyurea.
Step 1. 3,4-bis-(4-fluorophenylmethyl)thiophene.

The desired compound was prepared according to the method of Example 13, step 1, except substituting 3,4-dibromothiophene for 2-bromothiophene.
Step 2. (R)-N-(3-(3,4-bis-(4-fluorophenylmethyl)thien-2-yl)-1-methyl-2-propynyl)-N-hydroxyurea.

The desired compound was prepared according to the method of Example 36, except substituting 3,4-bis-(4-fluorophenylmethyl)thiophene, prepared as in step 1, for 3-(4-fluorophenylmethyl)thiophene, and using n-butyllithium instead of LDA. mp 128°–130° C. $^1$H NMR (DMSO-d$_6$) δ1.34 (d, J=7.5 Hz, 3H), 3.75 (s, 2H), 3.87 (s, 2H), 5.13 (q, J=7 Hz, 1H), 6.87 (s, 2H), 7.05 (m, 7H), 7.16 (m, 2H), 9.34 (s, 1H). MS (DCI/NH$_3$) m/e 444 (M+NH$_4$)$^+$, 427 (M+H)$^+$. Anal calcd for C$_{23}$H$_{20}$FN$_2$O$_2$S: C, 64.77; H, 4.73; N, 6.57. Found: C, 65.19; H, 4.65; N, 6.15.

EXAMPLE 39

Preparation of (R)-N-(3-(5-(4-fluorophenylmethyl)-5-methylthien-2-yl)-1-methyl-2-propynyl)-N-hydroxyurea.
Step 1. 2-iodo-3-(4-fluorophenylmethyl)thiophene.

To a solution of 3-(4-fluorophenylmethyl)thiophene (1.16 g, 6.04 mmol) in 1:1 CHCl$_3$/methanol was added N-iodosuccinimide (1.70 g, 7.53 mmol). The reaction mixture was stirred for 3 hours, and then was diluted with CH$_2$Cl$_2$. The organic phase was extracted with saturated aqueous NaHCO$_3$ and brine, dried over MgSO$_4$, filtered, and concentrated in vacuo to give 1.83 g of 2-iodo-3-(4fluorophenylmethyl)thiophene which was used without further purification.

Step 1. 2-methyl-3-(4-fluorophenylmethyl)thiophene.

The 2-iodo-3-(4-fluorophenylmethyl)thiophene prepared in step 1 was taken up in ether and methylmagnesium bromide (3.0M in ether, 2.42 mL, 7.26 mmol) and dichloro[1,3-bis(diphenylphosphino)propane]nickel(II) (164 mg, 0.302 mmol) were added and the reaction mixture was stirred for 17 hours at ambient temperature. The reaction mixture was quenched with saturated aqueous NH$_4$Cl and extracted with ethyl acetate. The organic phase was washed with 1N aqueous H$_3$PO$_4$, saturated aqueous NaHCO$_3$, saturated aqueous Na$_2$S$_2$O$_3$, and brine, dried over MgSO$_4$, filtered, and concentrated in vacuo. Chromatography on silica gel (10% ethyl acetate/hexane) gave 2-methyl-3-(4-fluorophenylmethyl)thiophene (602 mg, 48%).

Step 3. (R)-N-(3-(5-(4-fluorophenylmethyl)-5-methylthien-2-yl)-1-methyl-2-propynyl)-N-hydroxyurea.

The desired compound was prepared according to the method of Example 19, steps 3 and 4, except substituting 2-methyl-3-(4-fluorophenylmethyl)thiophene, prepared as in step 2, for 2-(4-chlorophenylmethyl)thiophene. $^1$H NMR (DMSO-d$_6$) δ1.31 (d, J=7.5 Hz, 3H), 2.33 (s, 3H), 3.80 (s, 2H), 5.09 (q, J=7.5 Hz, 1H), 6.52 (bs, 2H), 6.93 (s, 1H), 7.10 (m, 2H), 7.21 (m, 2H), 9.31 (s, 1H). MS (DCI/NH$_3$) m/e 350 (M+NH$_4$)$^+$, 333 (M+H)$^+$. Anal calcd for C$_{17}$H$_{17}$FN$_2$O$_2$S: C, 61.43; H, 5.15; N, 8.43. Found: C, 62.09; H, 5.19; N, 7.74.

EXAMPLE 40

Preparation of (R)-N-(3-(5-(4-biphenylhydroxymethyl)-5-methylthien-2-yl)-1-methyl-2-propynyl)-N-hydroxyurea.

The desired compound was prepared according to the method of Example 26, except substituting 4-biphenylcarboxaldehyde for 4-fluorobenzaldehyde. mp 120°–122° C. $^1$H NMR (DMSO-d$_6$) δ1.32 (d, J=7 Hz, 3H), 5.11 (q, J=7 Hz, 1H), 6.39 (d, J=4.2 Hz, 1H), 6.54 (s, 2H), 6.82 (dd, J=3.7 Hz, J=0.7 Hz, 1H), 7.06 (d, J=3.7 Hz, 1H), 7.35 (m, 1H), 7.46 (m, 4H), 7.65 (m, 4H), 9.32 (s, 1H). MS (DCI/NH$_3$) m/e 410 (M+NH$_4$)$^+$, 393 (M+H)$^+$. Anal calcd for C$_{22}$H$_{20}$N$_2$O$_3$S: C, 67.33; H, 5.14; N, 7.14. Found: C, 67.07; H, 5.11; N, 6.98.

EXAMPLE 41

Preparation of (R)-N-(3-(5-(4-biphenylmethyl)thien-2-yl)-1-methyl-2-propynyl)-N-hydroxyurea.

Step 1. 2-iodo-5-(4-biphenylhydroxymethyl)thiophene

The desired compound was prepared according to the method of Example 24, step 1, except substituting 4-biphenylcarboxaldehyde for 4-pyridinecarboxaldehyde.

Step 2. 2-iodo-5-(4-biphenylmethyl)thiophene.

To a solution of 2-iodo-5-(4-biphenylhydroxymethyl)thiophene (1.96 g, 5.0 mmol), prepared as in step 1, in dichloroethane (30 mL), was added sodium cyanoborohydride (2.2 g, 35 mmol), and ZnI$_2$ (2.0 g, 6.3 mmol). The reaction mixture was stirred for 6 hours at ambient temperature and then was filtered through a pad of celite. The filter cake was rinsed with CH$_2$Cl$_2$ and hexane, and the flitrate was concentrated in vacuo. Pure 2-iodo-5-(4-biphenylmethyl)thiophene (1.7 g) was obtained by chromatography on silica gel (3% ethyl acetate/hexane) and recrystallization from hexane/ethyl acetate.

Step 3. (R)-N-(3-(5-(4-biphenylmethyl)thien-2-yl)-1-methyl-2-propynyl)-N-hydroxyurea.

The desired compound was prepared as described in Example 13, step 4, except substituting 2-iodo-5-(4-biphenylmethyl)thiophene, prepared as in step 2, for 2-iodo-5-(4-fluorophenylmethyl)thiophene. mp 152°–153° C. $^1$H NMR (DMSO-d$_6$) δ1.32 (d, J=7 Hz, 3H), 4.17 (s, 2H), 5.11 (q, J=7 Hz, 1H), 6.53 (s, 2H) 6.86 (d, J=3.7 Hz, 1H), 7.09 (d, J=3.7 Hz, 1H), 7.36 (m, 3H), 7.46 (m, 2H), 7.63 (m, 4H), 9.32 (s, 1H). MS (DCI/NH$_3$) m/e 394 (M+NH$_4$)$^+$, 377 (M+H)$^+$. Anal calcd for C$_{22}$H$_{20}$N$_2$O$_2$S: C, 70.19; H, 5.35; N, 7.44. Found: C, 70.10; H, 5.27; N, 7.31.

EXAMPLE 42

Preparation of (R)-N-(3-(5-(thiazo-4-ylmethyl)thien-2-yl)-1-methyl-2-propynyl)-N-hydroxyurea.

Step 1. 2-(thiazo-4-ylmethyl)thiophene.

To a suspension of 4-chloromethylthiazole hydrochloride (3.41 g, 20.0 mmol) in THF (50 mL) was added triethylamine (3.04 g, 30.0 mmol) in one portion and the suspension was stirred for 2 hours at ambient temperature. The solid was then faltered off and rinsed with THF. The combined flitrate and washings were cooled to –78° C. and a solution of 2-thienyllithium in THF (20.0 mmol), prepared as in Example 12, step 1, was added over 10 min. The reaction mixture was stirred for 1 hour at –78° C. and then 17 hours at ambient temperature. The reaction was quenched with saturated aqueous NH$_4$Cl and diluted with ether. The organic phase was separated, dried over MgSO$_4$, filtered, and concentrated in vacuo to give a maroon-colored oil. Chromatography on silica gel provided 2-(thiazo-4-ylmethyl)thiophene (0.325 g).

Step 2. (R)-N-(3-(5-(thiazo-4-ylmethyl)thien-2-yl)-1-methyl-2-propynyl)-N-hydroxyurea.

The desired compound was prepared according to the method of Example 19, steps 3 and 4, except substituting 2-(thiazo-4-ylmethyl)thiophene for 2-(4-chlorophenylmethyl)thiophene. mp 119.5°–124° C. $^1$H NMR (DMSO-d$_6$) δ1.33(d, J=7 Hz, 3H), 4.30 (s, 2H), 5.11 (q, J=7 Hz, 1H), 6.50 (bs, 2H), 6.83 (d, J=4 Hz, 1H), 7.06 (d, J=4 Hz, 1H), 7.45 (d, J=2 Hz, 1H), 9.10 (d, J=2 Hz, 1H), 9.31 (s, 1H). MS (DCI/NH$_3$) m/e 325 (M+NH$_4$)$^+$, 308 (M+H)$^+$, 265. Anal calcd for C$_{13}$H$_{13}$N$_3$O$_2$S$_2$: C, 50.80; H, 4.26; N, 13.67. Found: C, 48.52; H, 4.19; N, 13.22.

EXAMPLE 43

Preparation of (R)-N-(3-(5-(benzo[b]thien-2-ylhydroxymethyl)thien-2-yl)-1-methyl-2-propynyl)-N-hydroxyurea.

The desired compound was prepared according to the method of Example 26, except substituting benzo[b]thiophene-2-carboxaldehyde for 4-fluorobenzaldehyde. mp 65°–70° C. $^1$H NMR (DMSO-d$_6$) δ1.34 (d, J=7 Hz, 3H), 5.12 (q, J=7 Hz, 1H), 6.28 (d, J=5 Hz, 1H), 6.51 (bs, 2H), 6.84 (d, J=5 Hz, 1H), 6.95 (m, 1H), 7.09 (d, J=4 Hz, 1H), 7.27–7.39 (m, 3H), 7.78 (m, 1H), 7.90 (m, 1H), 9.32 (s, 1H). MS (FAB (+)) m/e 373 (M+1), 154. Anal calcd for C$_{18}$H$_{16}$N$_2$O$_3$S$_2$: C, 58.05 H, 4.33; N, 7.52. Found: C, 57.87; H, 4.06 N, 7.38.

EXAMPLE 44

Preparation of (R)-N-(3-(5-(benzo[b]thien-2-ylmethyl)thien-2-yl)-1-methyl-2-propynyl)-N-hydroxyurea.

The desired compound was prepared according to the method of Example 41, steps 2 and 3. except substituting 2-iodo-5-(benzo[b]thien-2-ylhydroxymethyl)thiophene, prepared as in Example 43, for 2-iodo-5-(4-biphenylhydroxymethyl)thiophene. mp 157°–159° C. $^1$H NMR (DMSO-d$_6$) δ1.33 (d, J=7 Hz, 3H), 4.97 (s, 2H), 5.12 (q, J=7 Hz, 1H), 6.50 (s, 2H), 6.95 (d, J=4 Hz, 1H), 7.11 (d, J=4 Hz, 1H), 7.25 (m, 1H), 7.32 (m, 2H), 7.77 (m, 1H), 7.87 (m, 1H), 9.32 (s, 1H). MS (FAB (+)) m/e 357 (M+1), 281,147. Anal calcd for $C_{18}H_{16}N_2O_2S_2$: C, 60.65 H, 4.52; N, 7.86. Found: C, 60.72; H, 4.39 N, 7.82.

EXAMPLE 45

Preparation of (R)-N-(3-(3-(4-fluorophenylmethoxymethyl)thien-2-yl)-1-methyl-2-propynyl)-N-hydroxyurea.

The desired compound was prepared according to the method of Example 33, except substituting 3-thiophenemethanol for 2-thiophenemethanol. mp 94°–95° C. $^1$H NMR (DMSO-$d_6$) δ1.34 (d, J=7.5 Hz, 3H), 4.48 (s, 2H), 4.52 (s, 2H), 5.15 (q, J=7.5 Hz, 1H), 6.59 (s, 2H), 7.10 (d, J=6 Hz, 1H), 7.18 (m, 2H), 7.39 (m, 2H), 7.52 (d, J=6 Hz, 1H), 9.38 (s, 1H). MS (DCI/NH$_3$) m/e 366 (M+NH$_4$)$^+$, 349 (M+H)$^+$. Anal calcd for $C_{17}H_{17}FN_2O_3S$: C, 58.60; H, 4.92; N, 8.04. Found: C, 58.81; H, 4.72; N, 7.99.

EXAMPLE 46

Preparation of (R)-N-(3-(5-(2-(4-chlorophenyl)thiazo-4-ylmethyl)thien-2-yl)-1-methyl-2-propynyl)-N-hydroxyurea.

The desired compound was prepared according to the method of Example 33, except substituting 4-chloromethyl-2-(4-chlorophenyl)thiazole (Lancaster Synthesis, Inc., Windham, N.H.) for 4-fluorobenzyl bromide. mp 127°–128° C. $^1$H NMR (DMSO-$d_6$) δ1.35 (d, J=7.5 Hz, 3H), 4.65 (s, 2H), 4.75 (s, 2H), 5.13 (q, J=7.5 Hz, 1H), 6.55 (bs, 2H), 7.03 (d, J=4.5 Hz, 1H), 7.13 (d, J=4 Hz, 1H), 7.57 (m, 2H), 7.69 (s, 1H), 7.95 (m, 2H), 9.38 (s, 1H). MS (DCI/NH$_3$) m/e 448 (M+H)$^+$, 405. Anal calcd for $C_{20}H_{18}ClN_3O_3S_2$: C, 53.62; H, 4.05; N, 9.38. Found: C, 53.88; H, 4.21; N, 9.09.

EXAMPLE 47

Preparation of (R)-N-(3-(5-(1,2-dihydro-1-methyl-2-oxoquinolin-6-ylmethoxymethyl)thien-2-yl)-1-methyl-2-propynyl)-N-hydroxyurea.

The desired compound was prepared according to the method of Example 33, except substituting 1,2-dihydro-1-methyl-2-oxo-6-bromomethylquinoline (Medichem Research, Inc., Chicago Technology Park, Chicago, Ill.) for 4-fluorobenzyl bromide. $^1$H NMR (DMSO-$d_6$) δ1.36 (d, J=7.5 Hz, 3H), 3.62 (s, 3H), 4.58 (s, 2H), 4.69 (s, 2H), 5.14 (q, J=7.5 Hz, 1H), 6.57 (bs, 2H), 6.63 (d, J=9 Hz, 1H), 7.00 (d, J=4.5 Hz, 1H), 7.14 (d, J=4 Hz, 1H), 7.53 (d, J=9 Hz, 1H), 7.59 (dd, J=9, 2 Hz, 1H), 7.68 (d, J=2 Hz, 1H), 7.92 (d, J=9 Hz, 1H), 9.38 (s, 1H). MS (DCI/NH$_3$) m/e 412 (M+H)$^+$, 369. Anal calcd for $C_{21}H_{21}N_3O_4S$: C, 61.30; H, 5.14; N, 10.21. Found: C, 61.10; H, 5.22; N, 9.96.

EXAMPLE 48

Preparation of (R)-N-(3-(5-(thiazo-2-ylmethyl)thien-2-yl)-1-methyl-2-propynyl)-N-hydroxyurea.
Step 1. 2-thiopheneacetamide.

To a mixture of concentrated NH$_4$OH (100 mL) and ice was added 2-thiopheneacetyl chloride (13.0 g, 80.9 mmol). The desired compound crystallized from the reaction mixture. Recrystallization from hot water gave 2-thiopheneacetamide (8.08 g, 64% yield) as white crystals. mp 146°–147° C.
Step 2. 2-thiophenethioacetamide.

To a solution in THF (200 mL) of 2-thiopheneacetamide (4.04 g, 28.6 mmol), prepared as in step 1, was added P$_4$S$_{10}$ (12,7 g, 28.6 mmol), and the vigorously stirred reaction mixture was placed in a Bransonic 221 bath and irradiated with ultrasound for 30 min. The reaction mixture was filtered and the tiltrate was concentrated in vacuo. The crude product was taken up in CH$_2$Cl$_2$ and decanted from the solid residue. Pure 2-thiophenethioacetamide (2.45 g, 54% yield) was obtained by chromatography on silica gel (CH$_2$Cl$_2$).
Step 3. 2-(thiazo-2-ylmethyl)thiophene.

A solution of 2-thiophenethioacetamide (3.35 g, 21.3 mmol) in benzene (125 mL) was heated at reflux while 50% aqueous chloroacetaldehyde (6.62 g, 42.0 mmol) was added dropwise. The reaction mixture was heated for 2.5 hours at reflux, then left standing at −20° C. for 17 hours. After warming to reflux and heating for another hour, the reaction mixture was cooled to ambient temperature and the layers were separated. The organic layer was concentrated in vacuo to give 3.08 g of a dark oil. Chromatography on silica gel (CH$_2$Cl$_2$) gave 2-(thiazo-2-ylmethyl)thiophene (1.24 g). The aqueous phase was treated with decolorizing carbon and filtered. The filtrate was taken to pH 11 with 6N aqueous NaOH and extracted twice with ether. The combined ether layers were dried over KOH, filtered, and concentrated in vacuo to to give an additional 1.02 g of 2-(thiazo-2-ylmethyl)thiophene (total yield 2.26 g, 58%).
Step 4. (R)-N-{3-(5-(thiazo-2-ylmethyl)thien-2-yl)-1-methyl-2-propynyl)-N-hydroxyurea.

The desired compound was prepared according to the method of Example 19, steps 3 and 4, except substituting 2-(thiazo-2-ylmethyl)thiophene, prepared as in step 3, for 2-(4-chlorophenylmethyl)thiophene. mp 126°–131° C. $^1$H NMR (DMSO-$d_6$) δ1.34 (d, J=7 Hz, 3H), 4.56 (s, 2H), 5.13 (q, J=7 Hz, 1H), 6.51 (bs, 2H), 6.95 (m, 1H), 7.10 (d, J=4 Hz, 1H), 7.62 (d, J=4 Hz, 1H), 7.74 (d, J=4 Hz, 1H), 9.32 (s, 1H). MS (DCI/NH$_3$) m/e 325 (M+NH$_4$)$^+$, 308 (M+H)$^+$, 265. Anal calcd for $C_{13}H_{13}N_3O_2S_2$: C, 50.80; H, 4.26; N, 13.67. Found: C, 51.91; H, 4.32; N, 12.53.

EXAMPLE 49

Preparation of (R)-N-(3-(5-(4-fluorophenylmethyl)-2-bromothien-3-yl)-1-methyl-2-propynyl)-N-hydroxyurea.
Step 1. 2-bromo-5-(4-fluorophenylmethyl)thiophene.

To a −78° C. solution of LDA (19.3 mmol) in THF was added 2-bromothiophene (3.00 g, 18.4 mmol) and the reaction mixture was stirred for 15 min. A solution of 4-fluorobenzyl bromide (3.65 g, 19.3 mmol) in THF (1 mL) was added dropwise and the reaction mixture was warmed slowly to ambient temperature and stirred for 70 hours. The reaction mixture was poured into 0.5N aqueous HCl and extracted twice with ether. The combined organic layers were washed with saturated aqueous NaHCO$_3$ (2×) and brine, dried over MgSO$_4$, filtered, and concentrated in vacuo. Chromatography on silica gel (hexanes, then 3% ether/hexanes) gave 2-bromo-5-(4-fluorophenylmethyl)thiophene (2.25 g, 45%).
Step 2. (R)-N-(3-(5-(4-fluorophenylmethyl)-2-bromothien-3-yl)-1-methyl-2-propynyl)-N-hydroxyurea.

The desired compound was prepared according to the method of Example 36, except substituting 2-bromo-5-(4-fluorophenylmethyl)thiophene, prepared as in step 1, for 3-(4-fluorophenylmethyl)thiophene. $^1$H NMR (DMSO-$d_6$) δ1.36 (d, J=7.5 Hz, 3H), 4.12 (s, 2H), 5.12 (q, J=7.5 Hz, 1H), 6.56 (s, 2H), 6.96 (s, 1H), 7.15 (m, 2H), 7.32 (m, 2H), 9.34 (s, 1H). MS (DCI/NH$_3$) m/e 414 (M+NH$_4$)$^+$, 397 (M+H)$^+$. Anal calcd for $C_{16}H_{15}BrFN_2O_2S$: C. 48.37; H, 3.55; N, 7.05. Found: C, 48.56; H, 3.52; N, 7.05.

EXAMPLE 50

Preparation of (R)-N-(3-(5-phenylmethylthien-2-yl)-1-methyl-2-propynyl)-N-hydroxyurea.

The desired compound was prepared according to the method of Example 22, except substituting thiophene for 2-bromo-3-methylthiophene, and substituting benzyl bromide for 4-fluorobenzyl bromide. mp. 140°–142° C. $^1$H NMR (DMSO-$d_6$) δ1.32 (d, J=7 Hz, 3H), 5.11 (q, J=7 Hz, 1H), 4.12 (s, 2H), 6.50 (bs, 2H), 6.81 (m, 1H), 7.06 (d, J=4 Hz, 1H), 7.19–7.36 (m, 5H), 9.31 (s, 1H). MS (DCI/NH$_3$) m/e 318(M+NH$_4$)$^+$, 301 (M+H)$^+$, 225. Anal calcd for $C_{16}H_{16}N_2O_2S$: C, 63.98 H, 5.37; N, 9.33. Found: C, 63.74; H, 5.14; N, 9.14.

EXAMPLE 51

Preparation of N-(3-(5-(4-fluorophenylcarbonyl-O-methyloxime)thien-2-yl)-1-methyl-2-propynyl)-N-hydroxyurea.

A mixture of N-(3-(5-(4-fluorophenylcarbonyl)thien-2-yl)-1-methyl-2-propynyl)-N-hydroxyurea (100 mg, 0.30 mmol), prepared as in Example 14, methoxylamine hydrochloride (250 mg, 3.0 mmol), and sodium acetate trihydrate (410 mg, 3.0 mmol) in methanol (6 mL), was stirred under N$_2$ at ambient temperature for 28 hours. Additional portions (1.5 mmol each) of methoxylamine hydrochloride and sodium acetate trihydrate were added during this time. The methanol was removed in vacuo and the residue partitioned between ethyl acetate and and saturated aqueous NaHCO$_3$ solution. The organic phase was washed with brine, dried over MgSO$_4$, filtered, and concentrated in vacuo. Chromatography on silica gel (2% MeOH/CH$_2$Cl$_2$) provided N-(3-(5-(4-fluorophenylcarbonyl-O-methyloxime)thien-2-yl)-1-methyl-2-propynyl)-N-hydroxyurea (58.6 mg) as an oil. $^1$H NMR (DMSO-$d_6$) δ1.36 (d, J=7 Hz, 0.75H), 1.36 (d, J=7 Hz, 2.25H), 3.87 (s, 0.75H), 4.07 (s, 2.25H), 5.11 (overlaping q, J=7 Hz, 1H), 6.50 (bs, 2H), 6.68 (d, J=4 Hz, 0.25H), 6.99 (d, J=4 Hz, 0.75H), 7.13 (d, J=4 Hz, 0.75H), 7.22 (d, J=4 Hz, 0.25H), 7.32 (m, 2H), 7.43 (m, 0.5H), 7.53 (m, 1.5H), 9.39 (s, 0.25H), 9.41 (s, 0.75H). MS (DCI/NH$_3$) m/e 379(M+NH$_4$)$^+$, 362 (M+H)$^+$, 319.

EXAMPLE 52

Preparation of (S)-(–)-N-(1-butyn-3-yl)-N-hydroxyurea via resolution.

Step 1. N-(1-butyn-3-yl)-N-phenoxycarbonyl-O-[N-(9-fluorenylmethoxycarbonyl)-L-phenylalanyl]hydroxylamine.

A solution of dl-N-(1-butyn-3-yl)-N-hydroxyphenylcarbamate (2.30 g, 11.2 mmol), prepared by reaction of 3-butyn-1-ol with N,O-bis(phenoxycarbonyl)hydroxylamine, triphenylphosphine, and diethylazodicarboxylate as described in Scheme 3 and treatment of the resulting N,O-bis(phenoxycarbonyl) derivative with NH$_4$OH in methanol, in anhydrous methylene chloride (100 mL) at room temperature was treated with N-(9-fluorenylmethoxycarbonyl)-L-phenylalanine (5.18 g, 13.4 mmol) followed by dropwise addition of a solution of 1,3-dicyclohexylcarbodiimide (2.76 g, 13.4 mmol) in anhydrous methylene chloride (35 mL) over a period of 15 minutes. The mixture was stirred overnight at room temperature under nitrogen, diluted with ether (200 mL) and filtered. The filtrate was concentrated in vacuo and the residue was purified by flash chromatography (silica gel, 5% ether-toluene) to separate the diastereomers. The purification yielded 1.76 g (54%) of the faster eluting diastereomer (S configuration at the stereocenter adjacent to the triple bond) and 1.47 g (45%) of the slower eluting diastereomer (R configuration at the stereocenter adjacent to the triple bond).

Step 2. (S)-(–)-N-(1-butyn-3-yl)-N-hydroxyphenylcarbamate.

A solution of S diastereomer (1.54 g, 2.68 mmol) from step 1 above in dioxane (35 mL) was treated with concentrated ammonium hydroxide (3.4 mL, 51.0 mmol) and the stoppered mixture stirred at room temperature for 30 minutes. The resulting suspension was concentrated in vacuo and the residue partitioned between ethyl acetate and 5% hydrochloric acid. The mixture was filtered and the filter cake was washed with fresh ethyl acetate. The organic layer was washed once with brine, dried over MgSO$_4$, filtered, and concentrated in vacuo. The residue was purified by flash chromatograpy (silica gel, CH$_2$Cl$_2$ to 5% ether/CH$_2$Cl$_2$) to give 456 mg (83%) of (S)-(–)-N-(1-butyn-3-yl)-N-hydroxyphenylcarbamate as a heavy, colorless oil which solidified upon standing. mp. 75°–76° C. (from ether-hexane) $[α]_D$ –96.7° (c=1, CH$_2$Cl$_2$).

Step 3. (S)-(–)-N-(1-butyn-3-yl)-N-hydroxyurea.

A solution of (S)-(–)-N-(1-butyn-3-yl)-N-hydroxyphenylcarbamate (440 mg, 2.15 mmol), prepared as in step 2, in liquid ammonia (5.0 mL) at –78° C. was sealed in a pressure tube and stirred overnight at room temperature. The contents of the pressure tube were again chilled at –78° C., the tube opened and the ammonia was allowed to evaporate. The residue was triturated with a 1:1 mixture of ether-hexane, collected and recrystallized from ethyl acetate-hexane to afford 182 mg (66%) of (S)-(–)-N-(1-butyn-3-yl)-N-hydroxyurea. mp. 126.5°–128.5° C. $[α]_D$ –50.96° (c=1.04, CH$_3$OH).

EXAMPLE 53

Preparation of (R)-(+)-N-(1-butyn-3-yl)-N-hydroxyurea via resolution.

Step 1. (R)-(+)-N-(1-butyn-3-yl)-N-hydroxyphenylcarbamate.

The R diastereomer (1.47 g, 2.55 mmol) from Example 52, step 1 above, was treated ammonium hydroxide as described in Example 52, step 2, to afford 214 mg (41%) of (R)-(+)-N-(1-butyn-3-yl)-N-hydroxyphenylcarbamate after flash chromatography (silica gel, CH$_2$Cl$_2$ to 5% ether-CH$_2$Cl$_2$) and two recrystallizations from ether-hexane. mp. 75°–76° C. $[α]_D$ +76.1° (c=1, CH$_2$Cl$_2$).

Step 2. (R)-(+)-N-(1-butyn-3-yl)-N-hydroxyurea.

(R)-(+)-N-(1-butyn-3-yl)-N-hydroxyphenylcarbamate (314 mg, 1.53 mmol), prepared as in step 1, was subjected to ammonolysis in an identical manner as described in Example 52, step 3, to afford 98.8 mg (50%) of (R)-(+)-N-(1-butyn-3-yl)-N-hydroxyurea after two recrystallizations from ethyl acetate-hexane. mp. 120°–123° C. $[α]_D$ +49.17° (c=1, CH$_3$OH).

EXAMPLE 54

Preparation of R-(+)-N-(1-butyn-3-yl)-N-hydroxyurea.
Step 1. (2S-trans)-3-methyloxiranemethanol 4-methylbenzenesulfonate.

The epoxidation of trans-crotyl alcohol with TBHP and L-(+)-DIPT and sulfonylation of the resulting epoxide were performed exactly as described by Gao, Y., Hanson, R. M., Klunder, J. M., Ko, S. Y., Masamune, H., Sharpless, K. B., J. Am. Chem. Soc. 1987, 109, 5765–5780. After work-up the crude product was purifed on silica-gel column with methylene chloride-ethyl acetate (99:1 ) as eluent and finally recrystallized from ethyl ether/hexane to provide (2S-trans)-

3-methyloxiranemethanol 4-methylbenzenesulfonate (22% yield). mp. 63°–64° C., $\alpha_D$=–32.90° (c =2, CHCl$_3$).
Step 2. (R)-N,O-bis(phenoxycarbonyl)-N-(3-butyn-2-yl)hydroxylamine.

A solution of (2S-trans)-3-methyloxiranemethanol 4-methylbenzenesulfonate (484 mg; 2 mmol), prepared as in step 1, in dry THF (20 ml) was treated at –70° C. to –60° C. with n-BuLi (1.6M in hexane, 7.5 ml, 12 mmol) under an atmosphere of nitrogen. Glacial acetic acid (1 ml) was added after consumption of all the rosylate (monitored by TLC). After 15 min, sodium bicarbonate (600 mg) was added and the reaction mixture was allowed to warm to room temperature. After filtration through Celite, N,O-diphenoxycarbonylhydroxylamine (550 mg, 2.00 mmol) and triphenylphosphine (786 mg, 3.00 mmol) were added to the filtrate. The resulting mixture was treated with DEAD (0.5 ml, 3.0 mmol), taking care that the reaction temperature did not rise above ambient temperature. The reaction mixture was stirred at room temperature for 16 hours and then concentrated in vacuo. The residue was purifed by chromatography on silica-gel (10% ethyl acetate/hexane) to give (R)-N,O-bis(phenoxycarbonyl)-N-(3-butyn-2-yl)hydroxylamine- (contaminated with phenol).
Step 3. R-(+)-N-(1-butyn-3-yl)-N-hydroxyurea.

To a solution in methanol (20 mL) of the (R)-N,O-bis(phenoxycarbonyl)-N-(3-butyn-2-yl)hydroxylamine prepared in step 2 above was added concentrated ammonium hydroxide (80 ml). The mixture was stirred at room temperature for 48 hours. Concentration of the reaction mixture in vacuo and purifcation by chromatography on silica gel (10% ethanol/CH$_2$Cl$_2$) gave crystalline R-(+)-N-(1-butyn-3-yl)-N-hydroxyurea in 29% overall yield. mp. 127°–8° C. $[\alpha]_D$=+52.80° (c=1.2, MeOH).

EXAMPLE 55

Step 1. (S)-N,O-bis(phenoxycarbonyl)-N-(3-butyn-2-yl)hydroxylamine.

The desired compound was prepared according to the method of Example 54, steps 1 and 2, except carrying out the epoxidation described in Example 54, step 1, with TBHP and D(–)-DIPT. mp. 59°–60° C. (lit. $^1$) mp. 61°–62° C.). $[\alpha]_D$=+32.93° (c=3, CHCl$_3$).
Step 2. S-(–)-N-(1-butyn-3-yl)-N-hydroxyurea.

The desired compound was prepared in 23% overall yield according to the method of Example 54, step 3, except substituting (S)-N,O-bis(phenoxycarbonyl)-N-(3-butyn-2-yl)hydroxylamine, prepared as in step 1, for (R)-N,O-bis(phenoxycarbonyl)-N-(3-butyn-2-yl)hydroxylamine. mp. 126°–7° C. $[\alpha]_D$=–51.62° (c=0.96, MeOH).

The foregoing examples are merely illustrative of the invention and are not intended to limit the invention to the disclosed compounds. Variations and changes which are obvious to one skilled in the art are intended to be within the scope and nature of the invention which is defined in the appended claims.

We claim:
1. A compound of the formula:

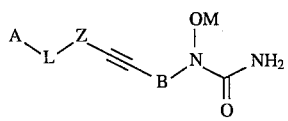

or a pharmaceutically acceptable salt thereof wherein
  M is selected from the group consisting of hydrogen, a pharmaceutically acceptable cation, and a pharmaceutically acceptable metabolically cleavable group;

B is a straight or branched divalent alkylene group of from one to twelve carbon atoms;

Z is thiazolyl, optionally substituted with
  alkyl of from one to six carbon atoms or
  haloalkyl of from one to six carbon atoms;

L is selected from the group consisting of
  (a) alkylene of from 1–6 carbon atoms,
  (b) alkenylene of from 2–6 carbon atoms,
  (c) alkynylene of from 2–6 carbon atoms,
  (d) hydroxyalkyl of 1–6 carbon atoms,
  (e) >C═O,
  (f) >C═N—OR$_1$, where R$_1$ is hydrogen or C$_1$–C$_6$ alkyl,
  (g) —(CHR$_1$)$_n$(CO)(CHR$_2$)$_m$, where n and m are independently selected from an integer from one to six and R$_1$ and R$_2$ are independently selected from hydrogen and C$_1$–C$_6$-alkyl,
  (h) —(CHR$_1$)$_n$C═NOR$_2$, where R$_1$, R$_2$ and n are as defined above;
  (i) —(CHR$_1$)$_n$ON═CR$_2$, where R$_1$, R$_2$ and n are as: defined above;
  (j) —(CHR$_1$)$_n$—O—(CHR$_2$)$_m$—, where R$_1$, R$_2$, n and m are as defined above,
  (k) —(CHR$_1$)$_n$—NR$_2$(CHR$_3$)$_m$—, where R$_1$, R$_2$, n and m are as defined above and R$_3$ is selected from hydrogen and C$_1$–C$_6$-alkyl;
  (l) —(CHR$_1$)$_n$—S—(CHR$_2$)$_m$—, where R$_1$, R$_2$, n and m are as defined above; and
  (m) —(CHR$_1$)$_n$—(SO$_2$)—(CHR$_2$)$_m$—, where R$_1$, R$_2$, n and m are as defined above;

A is carbocyclic aryl optionally substituted with
  alkyl of from one to six carbon atoms,
  haloalkyl of from one to six carbon atoms,
  hydroxyalkyl of from one to six carbon atoms,
  alkoxy of from one to twelve carbon atoms,
  alkoxyalkoxyl in which the two alkoxy portions may each independently contain from one to six carbon atoms,
  alkylthio of from one to six carbon atoms,
  hydroxy,
  halogen,
  cyano,
  amino,
  alkylamino of from one to six carbon atoms,
  dialkylamino in which the two alkyl groups may independently contain from one to six carbon atoms,
  alkanoylamino of from two to eight carbon atoms,
  N-alkanoyl-N-alkylamino in which the alkanoyl is of from two to eight carbon atoms and the alkyl group is of from one to six carbon atoms,
  alkylaminocarbonyl of from two to eight carbon atoms,
  dialkylaminocarbonyl in which the two alkyl groups are independently of from one to six carbon atoms,
  carboxyl,
  alkcoxycarbonyl or from two to eight carbon atoms,
  phenyl, optionally substituted with
    alkyl of from one to six carbon atoms,
    haloalkyl of from one to six carbon atoms,
    alkoxy of from one to six carbon atoms,
    hydroxy or
    halogen,
  phenoxy, optionally substituted with
    alkyl of from one to six carbon atoms,
    haloalkyl of from one to six carbon atoms,
    alkoxy of from one to six carbon atoms,
    hydroxy or
    halogen, and phenylthio, optionally substituted with
  alkyl of from one to six carbon atoms,
  haloalkyl of from one to six carbon atoms,
  alkoxy of from one to six carbon atoms,
  hydroxy or
  halogen.

2. A composition for inhibiting the biosynthesis of leukotrienes comprising an effective amount of a compound as defined by claim 1 in combination with a pharmaceutically acceptable carrier.

3. A method for inhibiting leukotriene biosynthesis in a mammal in need of such treatment, comprising administering to the mammal a therapeutically effective amount of a compound as defined by claim 1.

4. A compound or pharmaceutically acceptable salt thereof having the name
  (R)-N-{3-[-5-(4-fluorophenylmethyl)thiazo-2-yl]-1methyl-2-propynyl}-N-hydroxyurea.

* * * * *